US012655377B2

(12) United States Patent
Chang et al.

(10) Patent No.: US 12,655,377 B2
(45) Date of Patent: Jun. 16, 2026

(54) SURFACE-MODIFIED CELL CULTURE SUBSTRATES AND METHODS OF MODIFYING CELL CULTURE SUBSTRATES

(71) Applicant: CORNING INCORPORATED, Corning, NY (US)

(72) Inventors: Theresa Chang, Painted Post, NY (US); Paula Jean Dolley-Sonneville, Corning, NY (US); Paul Ernest Gagnon, Jr., Hudson, FL (US); Vinalia Tjong, Painted Post, NY (US); Yue Zhou, Horseheads, NY (US)

(73) Assignee: CORNING INCORPORATED, Corning, NY (US)

( * ) Notice: Subject to any disclaimer, the term of this patent is extended or adjusted under 35 U.S.C. 154(b) by 569 days.

(21) Appl. No.: 18/030,665

(22) PCT Filed: Oct. 7, 2021

(86) PCT No.: PCT/US2021/053888

§ 371 (c)(1),
(2) Date: Apr. 6, 2023

(87) PCT Pub. No.: WO2022/076639

PCT Pub. Date: Apr. 14, 2022

(65) Prior Publication Data

US 2023/0365907 A1 Nov. 16, 2023

Related U.S. Application Data

(60) Provisional application No. 63/089,933, filed on Oct. 9, 2020.

(51) Int. Cl.
*C12M 1/00* (2006.01)
*C12M 1/12* (2006.01)

(52) U.S. Cl.
CPC ............ *C12M 23/20* (2013.01); *C12M 25/14* (2013.01)

(58) Field of Classification Search
CPC ...... C12M 23/20; C12M 25/14; C12M 25/02; C12M 25/08
See application file for complete search history.

(56) References Cited

U.S. PATENT DOCUMENTS 1,143,460 A 6/1915 Stull
3,853,712 A 12/1974 House et al.
(Continued)

FOREIGN PATENT DOCUMENTS

CN 200940147 Y 8/2007
CN 101605460 A 12/2009
(Continued)

OTHER PUBLICATIONS

Machine Translation of WO 2016/072726 A2 (Year: 2025).*
(Continued)

*Primary Examiner* — Michael L Hobbs
(74) *Attorney, Agent, or Firm* — F. Brock Riggs

(57) ABSTRACT

A cell culture substrate is provided that includes a substrate lattice having an ordered array of fibers and pores disposed between the fibers. The ordered array of fibers includes a cell culture surface to support adherent or semi-adherent cells during cell culture. The cell culture substrate further includes a positive charge coating disposed on the cell culture surface to promote adhesion of cells to the cell culture surface.

16 Claims, 21 Drawing Sheets

(56) References Cited

U.S. PATENT DOCUMENTS 4,201,845 A 5/1980 Feder et al.
4,755,281 A 7/1988 Penick
4,833,083 A 5/1989 Saxena
4,994,388 A 2/1991 Hillegas et al.
5,012,503 A 4/1991 Nambu et al.
5,079,168 A 1/1992 Amiot
5,266,476 A 11/1993 Sussman et al.
5,501,971 A 3/1996 Freedman et al.
5,510,262 A 4/1996 Stephanopoulos et al.
5,759,830 A 6/1998 Vacanti et al.
5,840,777 A 11/1998 Eagles et al.
5,998,184 A 12/1999 Shi
6,054,142 A 4/2000 Li et al.
6,130,080 A 10/2000 Fuller
6,150,159 A 11/2000 Fry
6,284,284 B1 9/2001 Naughton
6,334,968 B1 1/2002 Shapiro et al.
6,875,605 B1 4/2005 Ma
6,995,013 B2 2/2006 Connelly et al.
7,122,371 B1 10/2006 Ma
7,449,331 B2 11/2008 Whitley
7,524,513 B2 4/2009 Hai-Quan et al.
7,674,837 B2 3/2010 Gaserod et al.
7,700,747 B2 4/2010 Sato
7,968,050 B2 6/2011 Vogt et al.
8,017,384 B2 9/2011 Tsai et al.
8,137,959 B2 3/2012 Castillo Fernandez
8,198,087 B2 6/2012 Bayon et al.
8,507,263 B2 8/2013 Asnaghi et al.
8,597,939 B2 12/2013 Castillo Fernandez
8,653,319 B2 2/2014 Amery et al.
8,721,963 B2 5/2014 Matthews et al.
8,951,574 B2 2/2015 Gehri et al.
8,951,784 B2 2/2015 Gould et al.
9,089,117 B2 7/2015 Grande et al.
9,175,259 B2 11/2015 Nankervis
9,198,997 B2 12/2015 Myntti et al.
9,217,129 B2 12/2015 Moretti et al.
9,220,810 B2 12/2015 Ma et al.
9,228,579 B2 1/2016 Stobbe
9,273,278 B2 3/2016 Lee et al.
9,617,506 B2 4/2017 Jones et al.
9,657,266 B2 5/2017 Kasuto et al.
9,677,038 B2 6/2017 Stobbe
9,694,037 B2 7/2017 Nataraj et al.
9,766,228 B2 9/2017 Puschmann et al.
9,957,485 B2 5/2018 Kapre
10,077,420 B2 9/2018 Blahut
10,494,421 B2 12/2019 Castillo
11,111,470 B2 9/2021 Ferrie et al.
11,118,151 B2 9/2021 Ferrie et al.
11,401,493 B2 8/2022 Ferrie et al.
11,434,460 B2 9/2022 Ferrie et al.
2002/0155594 A1 10/2002 Hsieh et al.
2004/0152149 A1 8/2004 Reid et al.
2004/0211747 A1 10/2004 Whitley
2005/0014774 A1 1/2005 Storer et al.
2008/0057561 A1 3/2008 Takahashi et al.
2008/0206735 A1 8/2008 Asgari
2009/0076530 A1 3/2009 Fukutomi et al.
2009/0196901 A1 8/2009 Guilak et al.
2009/0239298 A1 9/2009 Gerecht et al.
2009/0263601 A1 10/2009 Renn
2010/0196963 A1 8/2010 Naughton et al.
2010/0203638 A1 8/2010 Adachi et al.
2010/0216229 A1 8/2010 Kenney et al.
2011/0040226 A1 2/2011 Amery et al.
2011/0212493 A1 9/2011 Hirschel et al.
2011/0236256 A1 9/2011 Matthews et al.
2011/0250679 A1 10/2011 Chang
2011/0263021 A1* 10/2011 Stobbe ................ F04B 43/0736
435/243
2011/0275056 A1 11/2011 Antwiler
2012/0129257 A1 5/2012 Yu et al.
2012/0253071 A1 10/2012 Rau et al.
2013/0116571 A1 5/2013 Cox et al.
2013/0171710 A1 7/2013 Prebble
2014/0030805 A1 1/2014 Kasuto et al.
2014/0193901 A1 7/2014 Lee et al.
2014/0227769 A1 8/2014 Strobbe
2014/0243995 A1 8/2014 Kolewe et al.
2015/0299634 A1 10/2015 Drugmand et al.
2015/0322399 A1 11/2015 Purushothaman et al.
2016/0145567 A1 5/2016 Henry et al.
2016/0281045 A1 9/2016 Mccall et al.
2016/0304832 A1 10/2016 Hariri et al.
2017/0166859 A1 6/2017 Wang et al.
2017/0321178 A1 11/2017 Ling et al.
2018/0016547 A1 1/2018 Hagihara et al.
2018/0044622 A1 2/2018 Poon et al.
2018/0187139 A1 7/2018 Patel
2018/0187141 A1 7/2018 Cox et al.
2018/0195048 A1 7/2018 Rao
2018/0273891 A1 9/2018 Tanabe et al.
2018/0282678 A1 10/2018 Castillo et al.
2019/0062683 A1 2/2019 Nankervis et al.
2019/0134271 A1 5/2019 Seo et al.
2019/0275519 A1 9/2019 Castillo et al.
2019/0382709 A1 12/2019 Vang et al.
2020/0157493 A1 5/2020 Ginn et al.
2020/0248121 A1* 8/2020 Ferrie .................... C12M 25/04
2020/0248122 A1 8/2020 Ferrie et al.
2020/0248123 A1 8/2020 Ferrie et al.
2020/0248124 A1 8/2020 Ferrie et al.
2020/0255783 A1 8/2020 Ferrie et al.
2021/0024868 A1 1/2021 Ferrie et al.
2021/0115378 A1 4/2021 Fahmy
2021/0130761 A1 5/2021 Ferrie et al.

FOREIGN PATENT DOCUMENTS

CN 102250390 A 11/2011
CN 103113627 A 5/2013
CN 105492595 A 4/2016
CN 108315258 A 7/2018
DE 3536349 A1 4/1987
EP 0044624 A1 1/1982
EP 0300666 A1 1/1989
EP 0967273 A1 12/1999
EP 1245670 A2 10/2002
EP 2154241 A2 2/2010
EP 2553860 A1 2/2013
EP 2566950 A1 3/2013
EP 3452575 A1 3/2019
JP 62-171672 A 7/1987
JP 05-179381 A 7/1993
JP 2001-120255 A 5/2001
JP 2008-054521 A 3/2008
JP 2013-063283 A 4/2013
JP 2016-136868 A 8/2016
WO 88/00235 A1 1/1988
WO 92/07615 A1 5/1992
WO 98/50522 A1 11/1998
WO 00/05257 A1 2/2000
WO 01/03750 A1 1/2001
WO 2005/014774 A1 2/2005
WO 2005/023323 A1 3/2005
WO 2006/088029 A1 8/2006
WO 2011/123805 A1 10/2011
WO 2011/139957 A1 11/2011
WO 2012/140519 A2 10/2012
WO 2014/093444 A1 6/2014
WO 2014/133805 A1 9/2014
WO 2014/209856 A1 12/2014
WO 2014/209865 A1 12/2014
WO 2015/005349 A1 1/2015
WO WO-2016072726 A2 * 5/2016 ......... B01D 39/1623
WO 2016/200888 A1 12/2016
WO 2017/193075 A1 11/2017
WO 2017/204563 A1 11/2017
WO 2018/021367 A1 2/2018
WO 2018/051415 A1 3/2018
WO 2018/187808 A1 10/2018
WO 2019/090211 A1 5/2019

(56) References Cited

FOREIGN PATENT DOCUMENTS

| | | | |
|---|---|---|---|
| WO | 2019/104069 | A1 | 5/2019 |
| WO | 2019/175442 | A1 | 9/2019 |
| WO | 2019/206902 | A1 | 10/2019 |
| WO | 2020/163329 | A1 | 8/2020 |
| WO | 2021/091683 | A1 | 5/2021 |
| WO | 2021/108072 | A1 | 6/2021 |

OTHER PUBLICATIONS

Andersen et al., "Ionically Gelled Alginate Foams: Physical Properties Controlled by Operational and Macromolecular Parameter", American Chemical Society, Biomacromolecules, vol. 13, 2012, pp. 3703-3710.

Arboleya et al., "Competitive Adsorption Of Proteins With Methylcellulose And Hydroxypropyl Methylcellulose", Food Hydrocolloids, vol. 19, No. 3, May 2005, pp. 485-491.

Baker et al., "Deconstructing The Third Dimension—How 3D Culture Microenvironments Alter Cellular Cues", Journal of Cell Science, vol. 125, 2012, pp. 3015-3024.

Barbetta et al., "Porous Alginate Hydrogels: Synthetic Methods for Tailoring the Porous Texture", Biomacromolecules, vol. 10, 2009, pp. 2328-2337.

Baylon et al; "Past, Present and Future of Surgical Meshes: A Review"; Membranes 2017, 47, 17; 23 Pages doi:10.3390/membranes7030047.

Bokhari et al., "Emulsion-templated Porous Polymers As Scaffolds For Three Dimensional Cell Culture: Effect Of Synthesis Parameters On Scaffold Formation And Homogeneity", Journal of Materials Chemistry, vol. 17, Jul. 2007, pp. 4088-4094.

Cereijido, M., "Polarized monolayers formed by epithelial cells on a permeable and translucent support", The Journal of Cell Biology, 1978, vol. 77, No. 3, pp. 853-880.

Champagne et al. "Effect of Immobilization in Alginate on the Stability of Freeze-Dried Bffidobacterium longum", Bioscience Microflora, 1996, vol. 15(1), pp. 9-15.

Da Violante et al; "Evaluation of the Cytotoxicity Effect of Dimethyl Sulfoxide (DMSO) on Caco2/TC7 Colon Tumor Cell Cultures"; Biol. Pharm. Bull. 25 (12) pp. 1600-1603 (2002.

Dickinson, Eric, "Hydrocolloids At Interfaces And The Influence On The Properties Of Dispersed Systems", Food Hydrocolloids, vol. 17, No. 1, Jan. 2003, pp. 25-39.

Emmerling et al; "Rational Plasmid Design and Bioprocess Optimization to Enhance Recombinant Adeno-Associated Virus (AAV) Productivity in Mammalian Cells"; Biotechnol. J. 2016, 11, (2)290297.

Fang, Y. et al., "Rehydration of Dried Alginate Gel Beads: Effect of the Presence of Gelatin and Gum Arabic." Carbohydrate Polymers, vol. 86, pp. 1145-1150, Jun. 13, 2011.

Galvao et al; "Unexpected Low-Dose Toxicity of the Universal Solvent DMSO"; The FASEB Journal, Research Communication, vol. 28, (2014); pp. 1-14.

Gong et al; "The Physical and Chemical Properties of Alginate and Its Application in Tissue Engineering Research and Clinical Application"; China Tissue Engineering Research and Clinical Rehabilitation, vol. 11, No. 18 pp. 3613-3615 (Abstract).

Gunter et al. "Swelling and morphology of calcium pectinate gel beads obtained from Silene vulgaris callus modified pectins", Carbohydrate Polymers, 2014, vol. 103, pp. 550-557.

Hoch et al; "Chemical Tailoring of Gelatin to Adjust Its Chemical and Physical Properties for Functional Bioprinting"; J. Mater. Chem. B, 2013, 1,230; p. 5675-5685.

House et al; "Method for Bulk Culture of Animal Cells on Plastic Film"; Expreimental Cell Research 71 (1972) pp. 293-296.

Huang et al., "Research Trypsin-Induced Proteome Alteration During Cell Subculture In Mammalian Cells", Huang et al. Journal of Biomedical Science, vol. 17, No. 36, 2010, pp. 1-10.

Hwang et al., "Fabrication Of Three-Dimensional Porous Cell-Laden Hydrogel For Tissue Engineering", IOP Publishing, Biofabrication, vol. 2,035003, 2010, pp. 1-12.

Ji-Soo Lee et al: "Optimization of calcium pectinate gel beads for sustained-release of catechin using response surface methodology", International Journal of Biological Macromolecules., vol. 42, No. 4, Jan. 18, 2008 (Jan. 18, 2008), pp. 340-347, XP055543912.

Knight; "Multisurface Glass Roller Bodle for Growth of Animal Cells in Culture"; Applied Environmental Microbiology, vol. 33, No. 3, 1977, pp. 666-669.

Kuo et al., "Ionically Crosslinked Alginate Hydrogels As Sca!olds For Tissue Engineering: Part 1. Structure, Gelation Rate And Mechanical Properties", Biomaterials, vol. 22, 2001, pp. 511-521.

Kuo, S. M., et al., "Plasma-modified Nylon Meshes as Supports for Cell Culturing", Artificial Cells, Blood Substitutes, and Biotechnology, vol. 25, No. 6, 1997, pp. 551-562.

Lawrence, Benjamin J., "Mass Transfer In Porous Tissue Engineering Scaffolds", Oklahoma State University, 2008, 193 pages.

Lee et al., "Optimization of Calcium Pectinate Gel Beads for Sustained-Release of Catechin Using Response Surface Methodology", International Journal of Biological Macromolecules., vol. 42, No. 4, Jan. 18, 2008, pp. 340-347.

Lee et al; "Toxicity Evaluation of Ethanol Treatment During in Vitro Maturation of Procine Oocytes and Subsequent Embroyonic Development Following Parthenogenetic Activation and in Vitro Fertilization"; International Journal of Molecular Medicine; 34; pp. 1372-138 (2014.

Leo et al. "Effects of Sterilization Treatments on Some Properties of Alginate Solutions and Gels", Biotechnol. Prog., 1990, vol. 6, pp. 51-53.

Lesch et al; "Process Development of Adenoviral Vector Production in Fixed Bed Bioreactor: From Bench to Commercial Scale"; Human Gene Therapy, vol. 26, No. 8, (2015).

Liu et al., "Effect Of 3D Scaffold And Dynamic Culture Condition On The Global Gene Expression Profile Of Mouse Embryonic Stem Cells", Biomaterials; vol. 27, No. 36, Dec. 2006, pp. 5978-5989.

Lonza, "Protocol for Performing a Trypan Blue Viability Test Technical Reference Guide", Available Online at <https://web.archive.org/web/20180921014905/http://www.lonzabio.jp/catalog/pdf/ri/T204.pdf>, BioResearch, Sep. 21, 2018, 2 pages.

Moczulska et al; "Biological Characterization of Woven Fabric Using Two-And Three-Dimensional Cell Cultures"; Journal of Biomedical Materials Research A; Apr. 2012 vol. 100A, Issue 4, pp. 882-893 DOI: 10.1002/jbm.a.34023.

Moroni et al; "3D Fiber-Deposited Scaffolds for Tissue Engineering: Influence of Pores Geometry and Architecture on Dynamic Mechanical Properties"; Biomaterials, vol. 27, 2006, pp. 974-985.

Mseka et al., "ADF/Cofilin Family Proteins Control Formation Of Oriented Actin-filament Bundles In The Cell Body To Trigger Fibroblast Polarization", Journal of Cell Science, vol. 120, 2007, pp. 4332-4344.

Munarin et al. "Sterilization treatments on polysaccharides: Effects and side effects on pectin", Food Hydrocolloids, 2013, vol. 31, pp. 74-84.

Nasatto et al., "Methylcellulose, a Cellulose Derivative with Original Physical Properties and Extended Applications", Polymers, vol. 7, 2015, pp. 777-803.

Neethu et al., "Pectin/carboxymethyl cellulose/microfibrillated cellulose composite scaffolds for tissue engineering", Carbohydrate Polymers, vol. 98, No. 1, Jul. 7, 2013, pp. 877-885.

Oberdoerster et al; "Differential Effect of Ethanol on PC12 Cell Death"; The Journal of Pharmacology and Experimental Therapeutics; vol. 287, No. 1; pp. 359-365 (1998.

Rainger et al; "A Novel System for Investigating the Ability of Smooth Muscle Cells and Fibroblasts to Regulate Adhesion of Flowing Leukocytes to Endothelial Cells"; Journal of Immimmunological Methods; 255 (2001) 73-82.

Rodenhizer et al; "Development of Tracer: Tissue Roll for Analysis of Cellular Environment and Response"; Biofabrication, 8 (045008) 18 Pages.

Santagapita, P. et al., "Formulation and Drying of Alginate Beads for Controlled Release and Stabilization of Invertase." Biomacromolecules vol. 12, pp. 3147-3155, Aug. 18, 2011.

Simon et al; "Polymer-Based Mesh as Supports for Multi-Layered 3D Cell Culture and Assays"; Biomaterials; 35(1); 2014; pp. 259-268 doi:10.1016/j.biomaterials.2013.09.049.

(56) References Cited

OTHER PUBLICATIONS

Simon, K. A., et al., "Disulfide-Based Diblock Copolymer Worm Gels: A Wholly-Synthetic Thermoreversible 3D Matrix for Sheet-Based Cultures", Biomacromolecules, vol. 16, No. 12, 2015, pp. 3952-3958.
Srivastava et al., "Development of a Novel Polygalacturonic Acid-Gelatin Blend Scaffold Fabrication and Biocompatibility Studies for Tissue-Engineering Applications", International Journal of Polymeric Materials, vol. 61, No. 9, 2012, pp. 679-698.
Stanley et al., "Texture-Structure Relationships In Foamed Dairy Emulsions", Food Research International, vol. 29, No. 1, 1996, pp. 1-13.
Tapani et al; "Toxicity of Ethanol in Low Concentrations"; Acta Radiologica; 37:6; pp. 923-926; (1996).
Thuenauer, R., et al., "Microfluidic approaches for epithelial cell layer culture and characterisation", The Analyst, vol. 139, No. 13, 2014, pp. 3206-3218.
Tsai et al., "Expansion Of Human Mesenchymal Stem Cells In Fibrous Bed Bioreactor", Biochemical Engineering Journal, 2015, pp. 1-7.
Vreeker, R. et al., "Drying and Rehydration of Calcium Alginate Gels." Food Biophysics, vol. 3, pp. 361-369, Jun. 26, 2008.
Zmora et al., "Tailoring The Pore Architecture In 3-d Alginate Scaffolds By Controlling The Freezing Regime During Fabrication", Biomaterials, vol. 23, 2002, pp. 4087-4094.

* cited by examiner

SURFACE-MODIFIED CELL CULTURE SUBSTRATES AND METHODS OF MODIFYING CELL CULTURE SUBSTRATES

CROSS-REFERENCE TO RELATED APPLICATIONS

This is a national stage application under 35 U.S.C. § 371 of International Application No. PCT/US2021/053888, filed Oct. 7, 2021, which claims the benefit of priority under 35 U.S.C. § 119 of U.S. Provisional Application Ser. No. 63/089,933 filed on Oct. 9, 2020, the contents of which are relied upon and incorporated herein by reference in their entirety.

FIELD OF THE DISCLOSURE

This disclosure general relates to substrates for culturing cells, as well as methods of making the same. In particular, the present disclosure relates to surface-modified cell culturing substrates and methods of modified cell culture substrates.

BACKGROUND

In the bioprocessing industry, large-scale cultivation of cells is performed for purposes of the production of hormones, enzymes, antibodies, vaccines, and cell therapies. Cell and gene therapy markets are growing rapidly, with promising treatments moving into clinical trials and quickly toward commercialization. However, one cell therapy dose can require billions of cells or trillions of viruses. As such, being able to provide a large quantity of cell products in a short amount of time is critical for clinical success.

A significant portion of the cells used in bioprocessing are anchorage dependent, meaning the cells need a surface to adhere to for growth and functioning. Traditionally, the culturing of adherent cells is performed on two-dimensional (2D) cell-adherent surfaces incorporated in one of a number of vessel formats, such as T-flasks, petri dishes, cell factories, cell stack vessels, roller bottles, and HYPERStack® vessels. These approaches can have significant drawbacks, including the difficulty in achieving cellular density high enough to make it feasible for large scale production of therapies or cells.

Alternative methods have been suggested to increase volumetric density of cultured cells. These include microcarrier cultures performed in stir tanks. In this approach, cells that are attached to the surface of microcarriers are subject to constant shear stress, resulting in a significant impact on proliferation and culture performance. Another example of a high-density cell culture system is a hollow fiber bioreactor, in which cells may form large three-dimensional aggregates as they proliferate in the interspatial fiber space. However, the cells growth and performance are significantly inhibited by the lack nutrients. To mitigate this problem, these bioreactors are made small and are not suitable for large scale manufacturing Another example of a high-density culture system for anchorage dependent cells is a packed-bed bioreactor system. In this this type of bioreactor, a cell substrate is used to provide a surface for the attachment of adherent cells. Medium is perfused along the surface or through the semi-porous substrate to provide nutrients and oxygen needed for the cell growth. For example, packed bed bioreactor systems that contain a packed bed of support or matrix systems to entrap the cells have been previously disclosed U.S. Pat. Nos. 4,833,083; 5,501,971; and 5,510,262. Packed bed matrices usually are made of porous particles as substrates or non-woven microfibers of polymer. Such bioreactors function as recirculation flow-through bioreactors. One of the significant issues with such bioreactors is the non-uniformity of cell distribution inside the packed bed. For example, the packed bed functions as depth filter with cells predominantly trapped at the inlet regions, resulting in a gradient of cell distribution during the inoculation step. In addition, due to random fiber packaging, flow resistance and cell trapping efficiency of cross sections of the packed bed are not uniform. For example, medium flows fast though the regions with low cell packing density and flows slowly through the regions where resistance is higher due to higher number of entrapped cells. This creates a channeling effect where nutrients and oxygen are delivered more efficiently to regions with lower volumetric cells densities and regions with higher cell densities are being maintained in suboptimal culture conditions.

Another significant drawback of packed bed systems disclosed in a prior art is the inability to efficiently harvest intact viable cells at the end of culture process. Harvesting of cells is important if the end product is cells, or if the bioreactor is being used as part of a “seed train,” where a cell population is grown in one vessel and then transferred to another vessel for further population growth. U.S. Pat. No. 9,273,278 discloses a bioreactor design to improve the efficiency of cell recovery from the packed bed during cells harvesting step. It is based on loosening the packed bed matrix and agitation or stirring of packed bed particles to allow porous matrices to collide and thus detach the cells. However, this approach is laborious and may cause significant cells damage, thus reducing overall cell viability.

An example of a packed-bed bioreactor currently on the market is the iCellis® by produced by Pall Corporation. The iCellis uses small strips of cell substrate material consisting of randomly oriented fibers in a non-woven arrangement. These strips are packed into a vessel to create a packed bed. However, as with similar solutions on the market, there are drawbacks to this type of packed-bed substrate. Specifically, non-uniform packing of the substrate strips creates visible channels within the packed bed, leading to preferential and non-uniform media flow and nutrient distribution through the packed bed. Studies of the iCellis® have noted a “systemic inhomogeneous distribution of cells, with their number increasing from top to bottom of fixed bed,” as well as a “nutrient gradient . . . leading to restricted cell growth and production,” all of which lead to the “unequal distribution of cells [that] may impair transfection efficiency.” (Rational plasmid design and bioprocess optimization to enhance recombinant adeno-associated virus (AAV) productivity in mammalian cells. *Biotechnol. J.* 2016, 11, 290-297). Studies have noted that agitation of the packed bed may improve dispersion, but would have other drawbacks (i.e., “necessary agitation for better dispersion during inoculation and transfection would induce increased shear stress, in turn leading to reduced cell viability.” Id.). Another study noted of the iCellis® that the uneven distribution of cells makes monitoring of the cell population using biomass sensors difficult (“ . . . if the cells are unevenly distributed, the biomass signal from the cells on the top carriers may not show the general view of the entire bioreactor.” Process Development of Adenoviral Vector Production in Fixed Bed Bioreactor: From Bench to Commercial Scale. *Human Gene Therapy*, Vol. 26, No. 8, 2015).

In addition, because of the random arrangement of fibers in the substrate strips and the variation in packing of strips between one packed bed and another of the iCellis®, it can be difficult for customers to predict cell culture performance, since the substrate varies between cultures. Furthermore, the packed substrate of the iCellis® makes efficiently harvesting cells very difficult or impossible, as it is believed that cells are entrapped by the packed bed.

While manufacturing of viral vectors for early-phase clinical trials is possible with existing platforms, there is a need for a platform that can produce high-quality product in greater numbers in order to reach late-stage commercial manufacturing scale. There is a need for cell culture matrices, systems, and methods that enable culturing of cells in a high-density format, with uniform cell distribution, and easily attainable and increased harvesting yields. In particular, there is a need for efficient cell culture surfaces for adherent-based cell culture that provides a beneficial surface for cell attachment and growth without trapping cells within the substrate so that the cells or cell by-products can be harvested.

SUMMARY

According to embodiments of this disclosure, a cell culture substrate is provided that includes a substrate lattice having an ordered array of fibers and pores disposed between the fibers. The ordered array of fibers includes a cell culture surface to support adherent or semi-adherent cells during cell culture. The cell culture surface further includes a positive charge coating disposed on the cell culture surface, where the positive charge coating promotes adhesion of cells to the cell culture surface.

In various aspects of some embodiments, the positive charge coating is a polymer coating. The positive charge coating can be selected from a group that includes a plasma-deposited coating, a silane-based amine coating, and a photoactive polymer coating. For the plasma-deposited coating, the plasma-deposited coating can include a diamine or a triamine. In some example, the plasma-deposited positive charge coating includes 1,3-diaminopropane. For the silane-based amine coating, the silane-based amine coating can include aminopropylsilsesquioxane (APS). For the photoactive polymer coating, the photoactive polymer coating can include at least one of an acrylamide, a methacrylamide, and an aminopropyl-methacrylamide. In some example embodiments, the photoactive polymer coating includes N-[3 (4-Benzoylbenzamido)propyl]-methacrylamide, a copolymer of acrylamide and N-[3 (4-Benzoylbenzamido)propyl]-methacrylamide, or a copolymer of N-[3 (4-Benzoylbenzamido)propyl]-methacrylamide and aminopropyl-methacrylamide. The photoactive polymer is grafted to the cell culture surface via exposure of the photoactive polymer to ultraviolet (UV) light. Other aspects of embodiments include a positive charge coating that includes a polycationic polymer, including at least one of polyethyeneimine and polyallylamine.

According to various embodiments, the substrate lattice comprises at least one of polystyrene, polyethylene terephthalate, polycarbonate, polyvinylpyrrolidone, polybutadiene, polyvinylchloride, polyethylene oxide, polypyrroles, and polypropylene oxide. The substrate lattice can include at least one of a molded polymer lattice sheet, a 3D-printed lattice sheet, and a woven mesh sheet. Each fiber of the ordered array of fibers can include a fiber diameter from about 50 μm to about 1000 μm, from about 50 μm to about 600 μm, from about 50 μm to about 400 μm, from about 100 μm to about 325 μm, or from about 150 μm to about 275 μm. The pores can include a pore diameter of from about 100 μm to about 1000 μm, from about 200 μm to about 900 μm, or from about 225 μm to about 800 μm. The pores can be arrayed in a regular pattern across the substrate lattice.

According to additional embodiments, a packed-bed bioreactor system for culturing cells is provided. The system includes a vessel having a media inlet, a media outlet, and an interior cavity disposed between and in fluid communication with the media inlet and media outlet. The system also includes a cell culture substrate disposed in the interior cavity between the media inlet and the media outlet in a packed-bed configuration. The cell culture substrate includes a plurality of porous disks in a stacked arrangement, each of the plurality of porous disks having a surface configured to culture cells thereon. The system further includes a positive charge coating disposed on the surface of each of the plurality of porous disks. The positive charge coating promotes adhesion of cells to the surface of the disks during cell culture.

According to some additional embodiments of this disclosure, a method of making a cell culture substrate is provided. The method includes providing a substrate lattice having an ordered array of pores disposed between connecting members of the lattice. The connecting members have a cell culture surface to support adherent or semi-adherent cells during cell culture. The method includes depositing a polymer coating on the cell culture surface of the substrate lattice. The polymer coating has a net positive charge to promote cell adhesion.

According to various aspects of embodiments of the method, the depositing of the polymer coating includes treating the substrate lattice using plasma. The polymer coating for the plasma treated substrate lattice can coating can include 1,3-diaminopropane. The polymer coating can include a silane-based amine coating, including aminopropylsilsesquioxane (APS). The polymer coating can also include a photoactive polymer coating. The photoactive polymer coating can include at least one of an acrylamide, a methacrylamide, and an aminopropyl-methacrylamide. In some specific embodiments, the photoactive polymer coating can include at least one of N-[3(4-Benzoylbenzamido)propyl]-methacrylamide, a copolymer of acrylamide and N-[3(4-Benzoylbenzamido)propyl]-methacrylamide, and a copolymer of N-[3(4-Benzoylbenzamido)propyl]-methacrylamide and aminopropyl-methacrylamide. In some aspect of the method embodiments, the depositing of the polymer coating includes at least one of (1) spray-coating the substrate lattice with the polymer coating and (2) soaking the substrate lattice in a solution comprising constituents of the polymer coating.

DETAILED DESCRIPTION

Figure 1A:
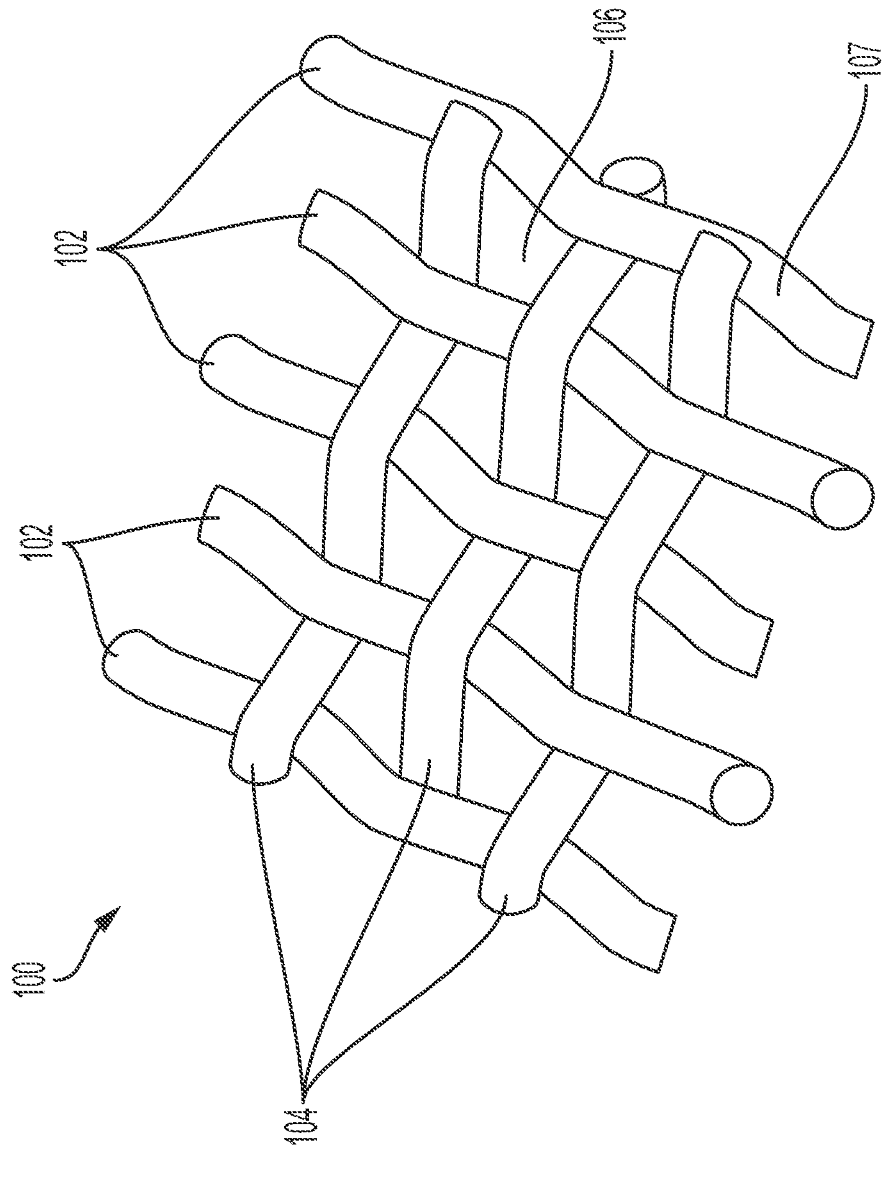
FIG. 1A shows a perspective view of a three-dimensional model of a cell culture substrate, according to one or more embodiments of this disclosure.

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments of the claimed invention.

Embodiments of this disclosure a cell culture substrate, including surface-modified cell culture substrates, methods of modifying cell culture substrates, as well as cell culture or bioreactor systems incorporating such substrates, and methods of culturing cells using such substrates and bioreactor systems.

In conventional large-scale cell culture bioreactors, different types of packed bed bioreactors have been used. Usually these packed beds contain porous matrices to retain adherent or suspension cells, and to support growth and proliferation. Packed-bed matrices provide high surface area to volume ratios, so cell density can be higher than in the other systems. However, the packed bed often functions as a depth filter, where cells are physically trapped or entangled in fibers of the matrix. Thus, because of linear flow of the cell inoculum through the packed bed, cells are subject to heterogeneous distribution inside the packed-bed, leading to variations in cell density through the depth or width of the packed bed. For example, cell density may be higher at the inlet region of a bioreactor and significantly lower nearer to the outlet of the bioreactor. This non-uniform distribution of the cells inside of the packed-bed significantly hinders scalability and predictability of such bioreactors in bioprocess manufacturing, and can even lead to reduced efficiency in terms of growth of cells or viral vector production per unit surface area or volume of the packed bed.

Another problem encountered in packed bed bioreactors disclosed in prior art is the channeling effect. Due to random nature of packed nonwoven fibers, the local fiber density at any given cross section of the packed bed is not uniform. Medium flows quickly in the regions with low fiber density (high bed permeability) and much slower in the regions of high fiber density (lower bed permeability). The resulting non-uniform media perfusion across the packed bed creates the channeling effect, which manifests itself as significant nutrient and metabolite gradients that negatively impact overall cell culture and bioreactor performance. Cells located in the regions of low media perfusion will starve and very often die from the lack of nutrients or metabolite poisoning. Cell harvesting is yet another problem encountered when bioreactors packed with non-woven fibrous scaffolds are used. Due to packed-bed functions as depth filter, cells that are released at the end of cell culture process are entrapped inside the packed bed, and cell recovery is very low. This significantly limits utilization of such bioreactors in bioprocesses where live cells are the products. Thus, the non-uniformity leads to areas with different exposure to flow and shear, effectively reducing the usable cell culture area, causing non-uniform culture, and interfering with transfection efficiency and cell release.

To address these and other problems of existing cell culture solutions, embodiments of the present disclosure provide cell growth substrates, matrices of such substrates, and/or packed-bed systems using such substrates that enable efficient and high-yield cell culturing for anchorage-dependent cells and production of cell products (e.g., proteins, antibodies, viral particles). Embodiments include a porous cell-culture matrix made from an ordered and regular array of porous substrate material that enables uniform cell seeding and media/nutrient perfusion, as well as efficient cell harvesting. Embodiments also enable scalable cell-culture solutions with substrates and bioreactors capable of seeding and growing cells and/or harvesting cell products from a process development scale to a full production size scale, without sacrificing the uniform performance of the embodiments. For example, in some embodiments, a bioreactor can be easily scaled from process development scale to product scale with comparable viral genome per unit surface area of substrate (VG/$cm^2$) across the production scale. The harvestability and scalability of the embodiments herein enable their use in efficient seed trains for growing cell populations at multiple scales on the same cell substrate. In addition, the embodiments herein provide a cell culture matrix having a high surface area that, in combination with the other features described, enables a high yield cell culture solution. In some embodiments, for example, the cell culture substrate and/or bioreactors discussed herein can produce $10^{16}$ to $10^{18}$ viral genomes (VG) per batch.

In one embodiment, a matrix is provided with a structurally defined surface area for adherent cells to attach and proliferate that has good mechanical strength and forms a highly uniform multiplicity of interconnected fluidic networks when assembled in a packed bed or other bioreactor. In particular embodiments, a mechanically stable, non-degradable woven mesh can be used as the substrate to support adherent cell production. The cell culture matrix disclosed herein supports attachment and proliferation of anchorage dependent cells in a high volumetric density format. Uniform cell seeding of such a matrix is achievable, as well as efficient harvesting of cells or other products of the bioreactor. In addition, the embodiments of this disclosure support cell culturing to provide uniform cell distribution during the inoculation step and achieve a confluent monolayer or multilayer of adherent cells on the disclosed matrix, and can avoid formation of large and/or uncontrollable 3D cellular aggregates with limited nutrient diffusion and increased metabolite concentrations. Thus, the matrix eliminates diffusional limitations during operation of the bioreactor. In addition, the matrix enables easy and efficient cell harvest from the bioreactor. The structurally defined matrix of one or more embodiments enables complete cell recovery and consistent cell harvesting from the packed bed of the bioreactor. Example embodiments of cell culture substrates and bioreactor systems incorporating such substrates are described in U.S. patent application Ser. No. 16/781,723, the content of which is incorporated herein in its entirety.

According to some embodiments, a method of cell culturing is also provided using bioreactors with the matrix for bioprocessing production of therapeutic proteins, antibodies, viral vaccines, or viral vectors.

In contrast to existing cell culture substrates used in cell culture bioreactors (i.e., non-woven substrates of randomly ordered fibers), embodiments of this disclosure include a cell culture substrate having a defined and ordered structure. The defined and order structure allows for consistent and predictable cell culture results. In addition, the substrate has an open porous structure that prevents cell entrapment and enables uniform flow through the packed bed. This construction enables improved cell seeding, nutrient delivery, cell growth, and cell harvesting. According to one or more particular embodiments, the matrix is formed with a substrate material having a thin, sheet-like construction having first and second sides separated by a relatively small thickness, such that the thickness of the sheet is small relative to the width and/or length of the first and second sides of the substrate. In addition, a plurality of holes or openings are formed through the thickness of the substrate. The substrate material between the openings is of a size and geometry that allows cells to adhere to the surface of the substrate material as if it were approximately a two-dimensional (2D) surface, while also allowing adequate fluid flow around the substrate material and through the openings. In some embodiments, the substrate is a polymer-based material, and can be formed as a molded polymer sheet; a polymer sheet with openings punched through the thickness; a number of filaments that are fused into a mesh-like layer; a 3D-printed substrate; or a plurality of filaments that are woven into a mesh layer. The physical structure of the matrix has a high surface-to-volume ratio for culturing anchorage dependent cells. According to various embodiments, the matrix can be arranged or packed in a bioreactor in certain ways discussed here for uniform cell seeding and growth, uniform media perfusion, and efficient cell harvest.

In some embodiments, the surface of the cell culture substrate can be modified for improved cell attachment and/or proliferation. Surface modifications can include coating the substrate surface in animal-derived gelatin or non-animal-derived gelatin replacements, which can support cell attachment and growth. Where animal-derived materials (e.g., gelatin) is undesirable, the surface of the cell culture substrate can be modified in other ways according to embodiments of this disclosure. For example, some embodiments include a plasma-treated cell culture surface, which can improve cell attachment to the substrate.

In one or more embodiments, the cell culture substrate is surface treated to provide a net positive charge to the substrate surface. One aspect of these embodiments includes a cell culture substrate having a plasma-deposited polymer on the surface. The plasma-deposited polymer can be provided, for example, by introducing an amine-containing small organic molecule into the plasma chamber to form the plasma-deposited polymer on the substrate surface. In another aspect of some embodiments, the cell culture substrate has a surface on which an amine-terminated silane molecule forms a silane polymer network on the cell culture substrate. In yet another aspect of embodiments, the cell culture substrate has a surface on which an amine-containing photo-reactive polymer was grafted by exposure of the photo-reactive polymer to ultraviolet (UV) light. These surface-modified cell culture substrate and methods of modifying the cell culture substrate surfaces can provide significant increases in the positive charge of the cell culture substrate surface, as well as good cell attachment. The cell attachment provided by embodiments of this disclosure is as good or better than that provided by similar substrates that have been gelatin coated and when using serum-free cell culture media.

According to one or more embodiments, the above surface modifications are performed on polymer cell culture substrates. In some preferred embodiments, the material of the cell culture substrate includes polyethylene terephthalate (PET). However, different polymeric materials compatible in cell culture applications are contemplated, including, for example, polystyrene, polyethylene terephthalate, polycarbonate, polyvinylpyrrolidone, polybutadiene, polyvinylchloride, polyethylene oxide, polypyrroles, and polypropylene oxide.

The advantages of embodiments disclosed herein include modified cell culture surfaces that are uniform (e.g., a uniform coating and/or distribution of positive charge on the surface) and allow for controlled coating density. In addition, the surface-modified substrates and methods allow for modified surfaces on cell culture substrates that have three-dimensional (3D) surfaces. For example, embodiments of cell culture substrates include substrates made of woven fibers and other three-dimensional porous scaffolds, and can complicated three-dimensional surfaces. However, the methods disclosed herein enable coating of such three-dimensional surfaces so that the entire surface can offer improved cell attachment and proliferation. Further, some of the methods of modifying surfaces disclosed herein can be applied to high-throughput and scalable manufacturing workflows, including, for example, roll-to-roll processes. In particular, methods using the amine terminated silane molecule to form a silane polymer network on the cell culture substrate, and methods using an amine-containing photo-reactive polymer grafted to the substrate can be adapted to roll-to-roll processing.

Figure 1B:
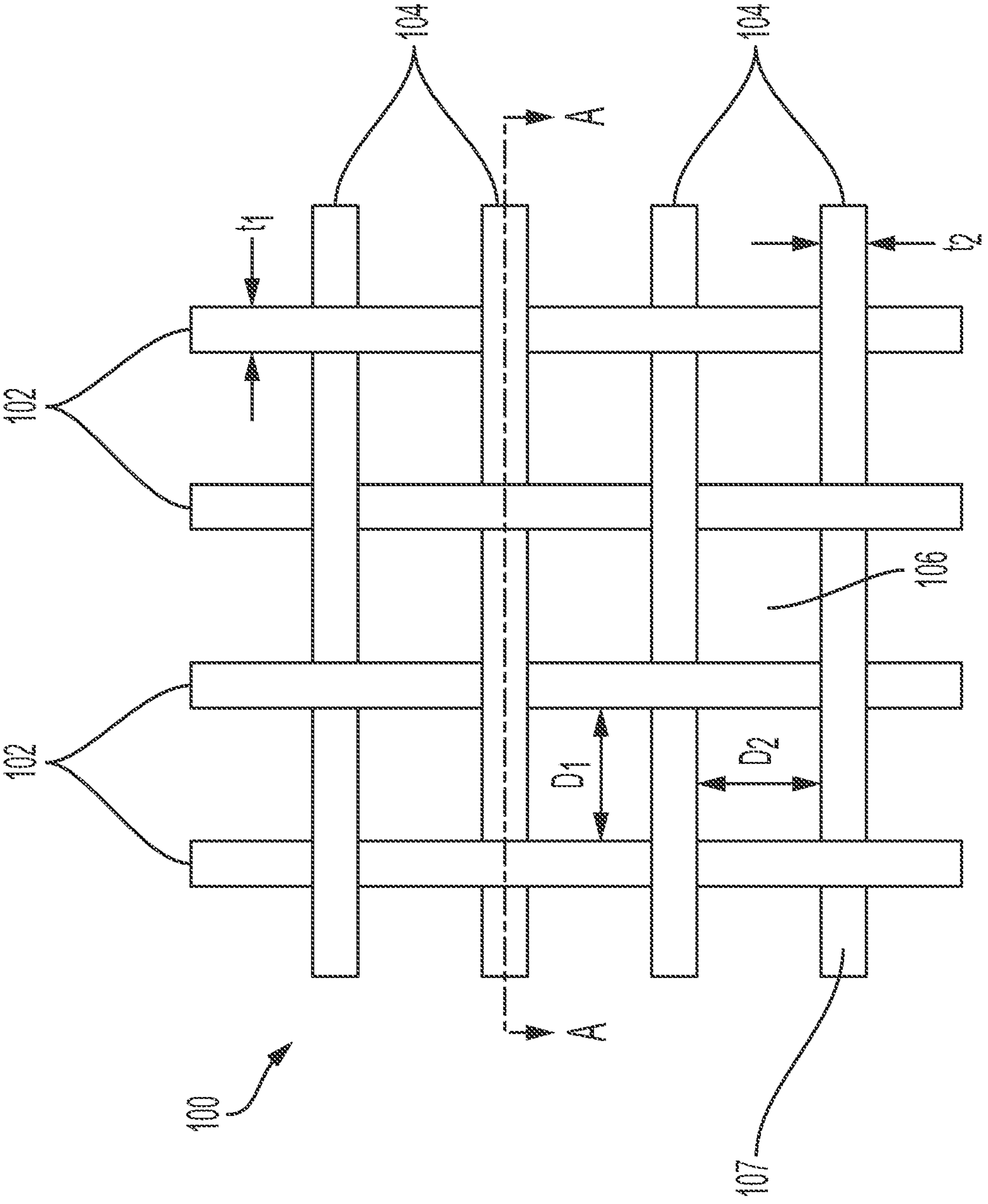
FIG. 1B is a two-dimensional plan view of the substrate of FIG. 1A.
Figure 1C:
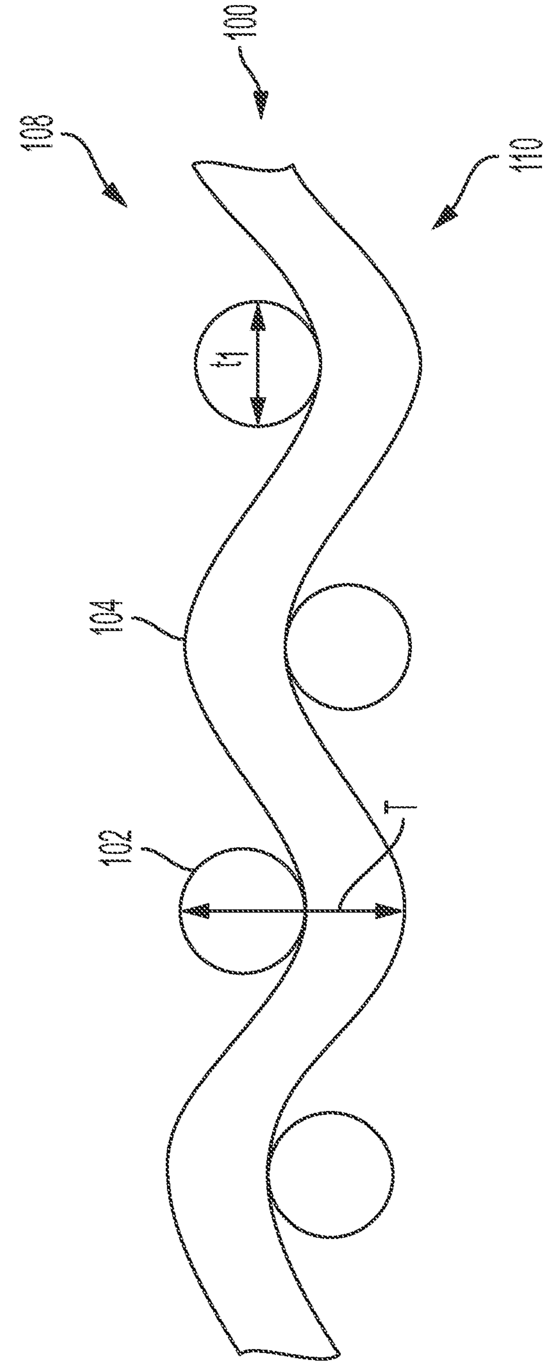
FIG. 1C is a cross-section along line A-A of the substrate in FIG. 1B.

FIGS. 1A and 1B show a three-dimensional (3D) perspective view and a two-dimensional (2D) plan view, respectively, of a cell culture substrate 100, according to an example of one or more embodiments of this disclosure. The cell culture substrate 100 is a woven mesh layer made of a first plurality of fibers 102 running in a first direction and a second plurality of fibers 104 running in a second direction. The woven fibers of the substrate 100 form a plurality of openings 106, which can be defined by one or more widths or diameters (e.g., $D_1$, $D_2$). The size and shape of the openings can vary based on the type of weave (e.g., number, shape and size of filaments; angle between intersecting filaments, etc.). A woven mesh may be characterized as, on a macro-scale, a two-dimensional sheet or layer. However, a close inspection of a woven mesh reveals a three-dimensional structure due to the rising and falling of intersecting fibers of the mesh. Thus, as shown in FIG. 1C, a thickness T of the woven mesh 100 may be thicker than the thickness of a single fiber (e.g., $t_1$). As used herein, the thickness T is the maximum thickness between a first side 108 and a second side 110 of the woven mesh. Without wishing to be bound by theory, it is believed that the three-dimensional structure of the substrate 100 is advantageous as it provides a large surface area for culturing adherent cells, and the structural rigidity of the mesh can provide a consistent and predictable cell culture matrix structure that enables uniform fluid flow.

In FIG. 1B, the openings 106 have a diameter $D_1$, defined as a distance between opposite fibers 102, and a diameter $D_2$, defined as a distance between opposite fibers 104. $D_1$ and $D_2$ can be equal or unequal, depending on the weave geometry. Where $D_1$ and $D_2$ are unequal, the larger can be referred to as the major diameter, and the smaller as the minor diameter. In some embodiments, the diameter of an opening may refer to the widest part of the opening. Unless otherwise specified, the opening diameter, as used herein, will refer to a distance between parallel fibers on opposite sides of an opening.

A given fiber of the plurality of fibers 102 has a thickness $t_1$, and a given fiber of the plurality of fibers 104 has a thickness $t_2$. In the case of fibers of round cross-section, as shown in FIG. 1A, or other three-dimensional cross-sections, the thicknesses $t_1$ and $t_2$ are the maximum diameters or thicknesses of the fiber cross-section. According to some embodiments, the plurality of fibers 102 all have the same thickness $t_1$, and the plurality of fiber 104 all have the same thickness $t_2$. In addition, $t_1$ and $t_2$ may be equal. However, in one or more embodiments, $t_1$ and $t_2$ are not equal such as when the plurality of fibers 102 are different from the plurality of fiber 104. In addition, each of the plurality of fibers 102 and plurality of fibers 104 may contain fibers of two or more different thicknesses (e.g., $t_{1a}$, $t_{1b}$, etc., and $t_{2a}$, $t_{2b}$, etc.). According to embodiments, the thicknesses $t_1$ and $t_2$ are large relative to the size of the cells cultured thereon, so that the fibers provide an approximation of a flat surface from the perspective of the cell, which can enable better cell attachment and growth as compared to some other solutions in which the fiber size is small (e.g., on the scale of the cell diameter). Due to three-dimensional nature of woven mesh, as shown in FIGS. 1A-1C, the 2D surface area of the fibers available for cell attachment and proliferation exceeds the surface area for attachment on an equivalent planar 2D surface.

In one or more embodiments, a fiber may have a diameter in a range of about 50 μm to about 1000 μm; about 100 μm to about 750 μm; about 125 μm to about 600 μm; about 150 μm to about 500 μm; about 200 μm to about 400 μm; about 200 μm to about 300 μm; or about 150 μm to about 300 μm. On a microscale level, due to the scale of the fiber compared to the cells (e.g., the fiber diameters being larger than the cells), the surface of monofilament fiber is presented as an approximation of a 2D surface for adherent cells to attach and proliferate. Fibers can be woven into a mesh with openings ranging from about 100 μm×100 μm to about 1000 μm×1000 μm. In some embodiments, the opening may have a diameter of about 50 μm to about 1000 μm; about 100 μm to about 750 μm; about 125 μm to about 600 μm; about 150 μm to about 500 μm; about 200 μm to about 400 μm; or about 200 μm to about 300 μm. These ranges of the filament diameters and opening diameters are examples of some embodiments, but are not intended to limit the possible feature sizes of the mesh according to all embodiments. The combination of fiber diameter and opening diameter is chosen to provide efficient and uniform fluid flow through the substrate when, for example, the cell culture matrix comprises a number of adjacent mesh layers (e.g., a stack of individual layers or a rolled mesh layer).

Factors such as the fiber diameter, opening diameter, and weave type/pattern will determine the surface area available for cell attachment and growth. In addition, when the cell culture matrix includes a stack, roll, or other arrangement of overlapping substrate, the packing density of the cell culture matrix will impact the surface area of the packed bed matrix. Packing density can vary with the packing thickness of the substrate material (e.g., the space needed for a layer of the substrate). For example, if a stack of cell culture matrix has a certain height, each layer of the stack can be said to have a packing thickness determined by dividing the total height of the stack by the number of layers in the stack. The packing thickness will vary based on fiber diameter and weave, but can also vary based the alignment of adjacent layers in the stack. For instance, due to the three-dimensional nature of a woven layer, there is a certain amount of interlocking or overlapping that adjacent layers can accommodate based on their alignment with one another. In a first alignment, the adjacent layers can be tightly nestled together, but in a second alignment, the adjacent layers can have zero overlap, such as when the lower-most point of the upper layer is in direct contact with the upper-most point of the lower layer. It may be desirable for certain applications to provide a cell culture matrix with a lower density packing of layers (e.g., when higher permeability is a priority) or a higher density of packing (e.g., when maximizing substrate surface area is a priority). According to one or more embodiments, the packing thickness can be from about 50 μm to about 1000 μm; about 100 μm to about 750 μm; about 125 μm to about 600 μm; about 150 μm to about 500 μm; about 200 μm to about 400 μm; about 200 μm to about 300 μm.

The cell culture substrate 100 has a substrate surface 107 defined by the collective surfaces of any and all constituent parts of the cell culture substrate 100. For example, the substrate surface 107 includes the cumulative surface area of the fibers 102, 104 in FIGS. 1A and 1B. The area of the substrate surface 107 defines the effective surface area available for cell adhesion and growth on that substrate. In a case where a cell culture matrix comprising a plurality of cell culture substrates (e.g., a multi-layered cell culture matrix having a plurality of woven mesh substrates in a stacked configuration), the available surface area of the cell culture matrix is the cumulative surface area of the plurality of cell culture substrates. The above structural factors can determine the surface area of a cell culture matrix, whether of a single layer of cell culture substrate or of a cell culture matrix having multiple layers of substrate). For example, in a particular embodiment, a single layer of woven mesh substrate having a circular shape and diameter of 6 cm can have an effective surface area of about 68 $cm^2$. The "effective surface area," as used herein, is the total surface area of fibers in a portion of substrate material that is available for cell attachment and growth. Unless stated otherwise, references to "surface area" refer to this effective surface area. According to one or more embodiments, a single woven mesh substrate layer with a diameter of 6 cm may have an effective surface area of about 50 $cm^2$ to about 90 $cm^2$; about 53 $cm^2$ to about 81 $cm^2$; about 68 $cm^2$; about 75 $cm^2$; or about 81 $cm^2$. These ranges of effective surface area are provided for example only, and some embodiments may have different effective surface areas. The cell culture matrix can also be characterized in terms of porosity, as discussed in the Examples herein.

The substrate mesh can be fabricated from monofilament or multifilament fibers of polymeric materials compatible in cell culture applications, including, for example, polystyrene, polyethylene terephthalate, polycarbonate, polyvinylpyrrolidone, polybutadiene, polyvinylchloride, polyethylene oxide, polypyrroles, and polypropylene oxide. Mesh substrates may have a different patterns or weaves, including, for example knitted, warp-knitted, or woven (e.g., plain weave, twilled weave, dutch weave, five needle weave).

As discussed herein, the surface chemistry of the substrate surface 107 can be modified to provide desired cell adhesion properties. Such modifications can be made through the chemical treatment of the polymer material of the substrate surface 107 or by grafting cell adhesion molecules to the substrate surface 107. Alternatively, the substrate surface 107 can be coated with thin layer of biocompatible hydrogels that demonstrate cell adherence properties, including, for example, collagen or Matrigel®. Alternatively, substrate surfaces 107 can be rendered with cell adhesive properties through the treatment processes with various types of plasmas, process gases, and/or chemicals known in the industry. In one or more embodiments, however, the substrate surface 107 is capable of providing an efficient cell growth surface without surface treatment.

Pre-coating of the substrate surface 107 with extracellular matrix proteins such as collagen, fibronectin, laminin, etc., can enhance the attachment of adherent cells. To avoid using animal-derived materials, synthetic polymeric cations such as polylysine or polyornithine can also be used as attachment promoting factors. To improve cell attachment and growth, vacuum-based plasma treatment with oxygen purging can be used.

According to preferred embodiments of this disclosure, HEK293 cells, which are often used in gene therapy, have been shown to attach better to positively charged coatings on polymer cell culture substrates (e.g., woven PET substrates) than to negatively charged coatings or less charged oxygen plasma treatment. Accordingly, the methods of this disclosure can introduce positive charges on a substrate surface 107 in a controlled manner efficiently and uniformly. Aided by the adaptability of cell culture substrate 100 to roll-to-roll processing, these methods can also be used in roll-to-roll process to benefit large scale manufacturing.

Figure 2A:
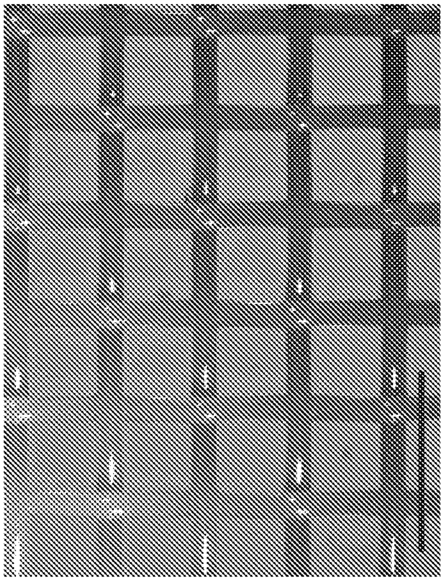
FIG. 2A shows an example of a cell culture substrate, according to some embodiments.
Figure 2B:
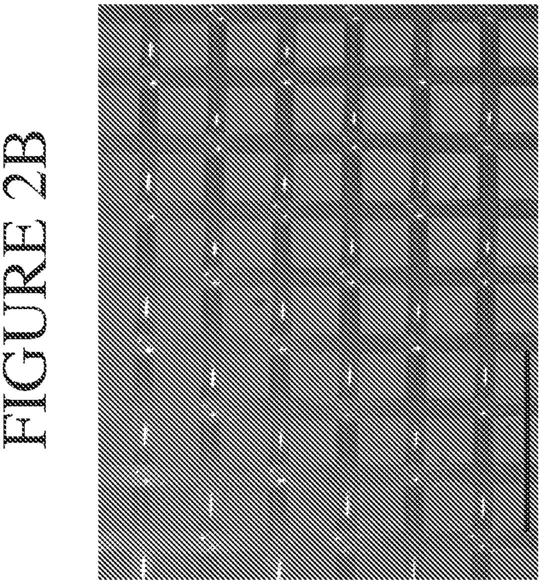
FIG. 2B shows an example of a cell culture substrate, according to some embodiments.
Figure 2C:
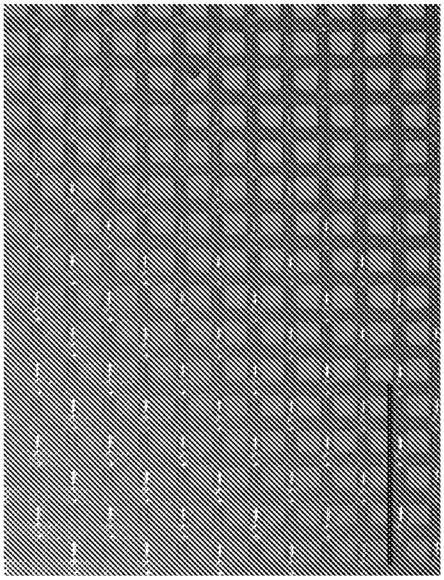
FIG. 2C shows an example of a cell culture substrate, according to some embodiments.

FIGS. 2A-2C show different examples of woven mesh according to some contemplated embodiments of this disclosure. The fiber diameter and opening size of these meshes are summarized in Table 1 below, as well as the approximate magnitude of increase in cell culture surface area provided by a single layer of the respective meshes relative to a comparable 2D surface. In Table 1, Mesh A refers to the mesh of FIG. 2A, Mesh B to the mesh of FIG. 2B, and Mesh C to the mesh of FIG. 2C. The three mesh geometries of Table 1 are examples only, and embodiments of this disclosure are not limited to these specific examples. Because Mesh C offers the highest surface area, it may be advantageous in achieving a high density in cell adhesion and proliferation, and thus provide the most efficient substrate for cell culturing. However, in some embodiments, it may be advantageous for the cell culture matrix to include a mesh with lower surface area, such as Mesh A or Mesh B, or a combination of meshes of different surface areas, to achieve a desired cell distribution or flow characteristics within the culture chamber, for example.

TABLE 1

Comparison of meshes in FIGS. 2A-2C, and the resulting increase in cell culture surface area as compared to a 2D surface.

| | Mesh A | Mesh B | Mesh C |
|---|---|---|---|
| Fiber diameter | 273 ± 3 μm | 218 ± 3 μm | 158 ± 3 μm |
| Mesh opening | 790 × 790 μm | 523 × 523 μm | 244 × 244 μm |
| Surface area increase of one layer of mesh compared to 2D surface | ×1.6 | ×1.8 | ×2.5 |

As shown by the above table, the three-dimensional quality of the meshes provides increased surface area for cell attachment and proliferation compared to a planar 2D surface of comparable size. This increased surface area aids in the scalable performance achieved by embodiments of this disclosure. For process development and process validation studies, small-scale bioreactors are often required to save on reagent cost and increase experimental throughput. Embodiments of this disclosure are applicable to such small-scale studies, but can be scaled-up to industrial or production scale, as well. For example, if 100 layers of Mesh C in the form of 2.2 cm diameter circles are packed into a cylindrical packed bed with a 2.2 cm internal diameter, the total surface area available for cells to attach and proliferate is equal to about 935 $cm^2$. To scale such bioreactor ten times, one could use a similar setup of a cylindrical packed bed with 7 cm internal diameter and 100 layers of the same mesh. In such a case, the total surface area would be equal 9,350 $cm^2$. In some embodiments, the available surface area is about 99,000 $cm^2$/L or more. Because of the plug-type perfusion flow in a packed bed, the same flow rate expressed in ml/min/$cm^2$ of cross-sectioned packed bed surface area can be used in smaller-scale and larger-scale versions of the bioreactor. A larger surface area allows for higher seeding density and higher cell growth density. According to one or more embodiments, the cell culture substrate described herein has demonstrated cell seeding densities of up to 22,000 cells/$cm^2$ or more. For reference, the Corning HyperFlask® has a seeding density on the order of 20,000 cells/$cm^2$ on a two-dimensional surface.

Another advantage of the higher surface areas and high cell seeding or growing densities is that the cost of the embodiments disclosed herein can be the same or less than competing solution. Specifically, the cost per cellular product (e.g., per cell or per viral genome) can be equal to or less than other packed bed bioreactors.

In a further embodiment of the present disclosure discussed below, a woven mesh substrate can be packed in a cylindrical roll format within the bioreactor (see FIGS. 14 and 15). In such an embodiment, the scalability of the packed bed bioreactor can be achieved by increasing the overall length of the mesh strip and its height. The amount of mesh used in this cylindrical roll configuration can vary based on the desired packing density of the packed bed. For example, the cylindrical rolls can be densely packed in a tight roll or loosely packed in a loose roll. The density of packing will often be determined by the required cell culture substrate surface area required for a given application or scale. In one embodiment, the required length of the mesh can be calculated from the packed bed bioreactor diameter by using following formula:

$$L = \frac{\pi(R^2 - r^2)}{t} \qquad \text{Equation 1}$$

where L is the total length of mesh required to pack the bioreactor (i.e., H in FIG. 14), R is the internal radius of packed bed culture chamber, r is the radius of an inner support (support 366 in FIG. 15) around which mesh is rolled, and t is the thickness of one layer of the mesh. In such a configuration, scalability of the bioreactor can be achieved by increasing diameter or width (i.e., W in FIG. 14) of the packed bed cylindrical roll and/or increasing the height H of the packed bed cylindrical roll, thus providing more substrate surface area for seeding and growing adherent cells.

By using a structurally defined culture matrix of sufficient rigidity, high-flow-resistance uniformity across the matrix or packed bed is achieved. According to various embodiments, the matrix can be deployed in monolayer or multilayer formats. This flexibility eliminates diffusional limitations and provides uniform delivery of nutrients and oxygen to cells attached to the matrix. In addition, the open matrix lacks any cell entrapment regions in the packed bed configuration, allowing for complete cell harvest with high viability at the end of culturing. The matrix also delivers packaging uniformity for the packed bed, and enables direct scalability from process development units to large-scale industrial bioprocessing unit. The ability to directly harvest cells from the packed bed eliminates the need of resuspending a matrix in a stirred or mechanically shaken vessel, which would add complexity and can inflict harmful shear stresses on the cells. Further, the high packing density of the cell culture matrix yields high bioprocess productivity in volumes manageable at the industrial scale.

Figure 3A:
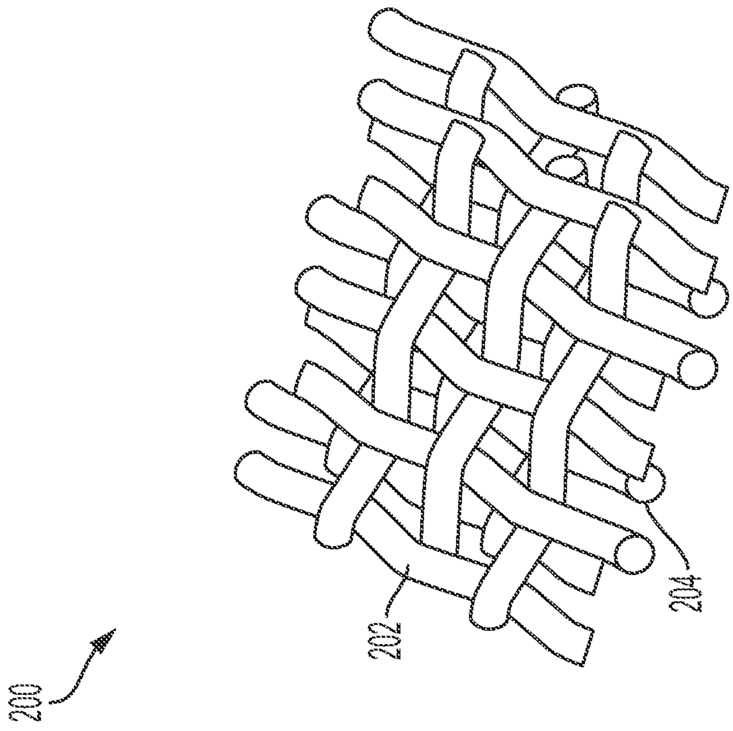
FIG. 3A shows a perspective view of a multilayer cell culture substrate, according to one or more embodiments.
Figure 3B:
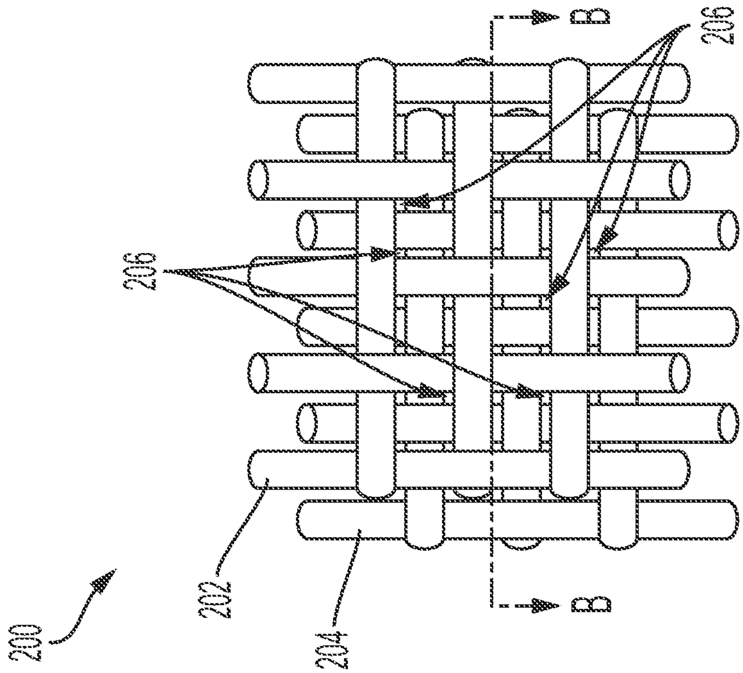
FIG. 3B shows a plan view of a multilayer cell culture substrate, according to one or more embodiments.

FIG. 3A shows an embodiment of the matrix with a multilayer substrate 200, and FIG. 3B is a plan view of the same multilayer substrate 200. The multilayer substrate 200 includes a first mesh substrate layer 202 and a second mesh substrate layer 204. Despite the overlapping of the first and second substrate layers 202 and 204, the mesh geometries (e.g., ratio of opening diameters to fiber diameters) is such that the openings of the first and second substrate layers 202 and 204 overlap and provide paths for fluid to flow through the total thickness of the multilayer substrate 200, as shown by the filament-free openings 206 in FIG. 3B.

Figure 4:
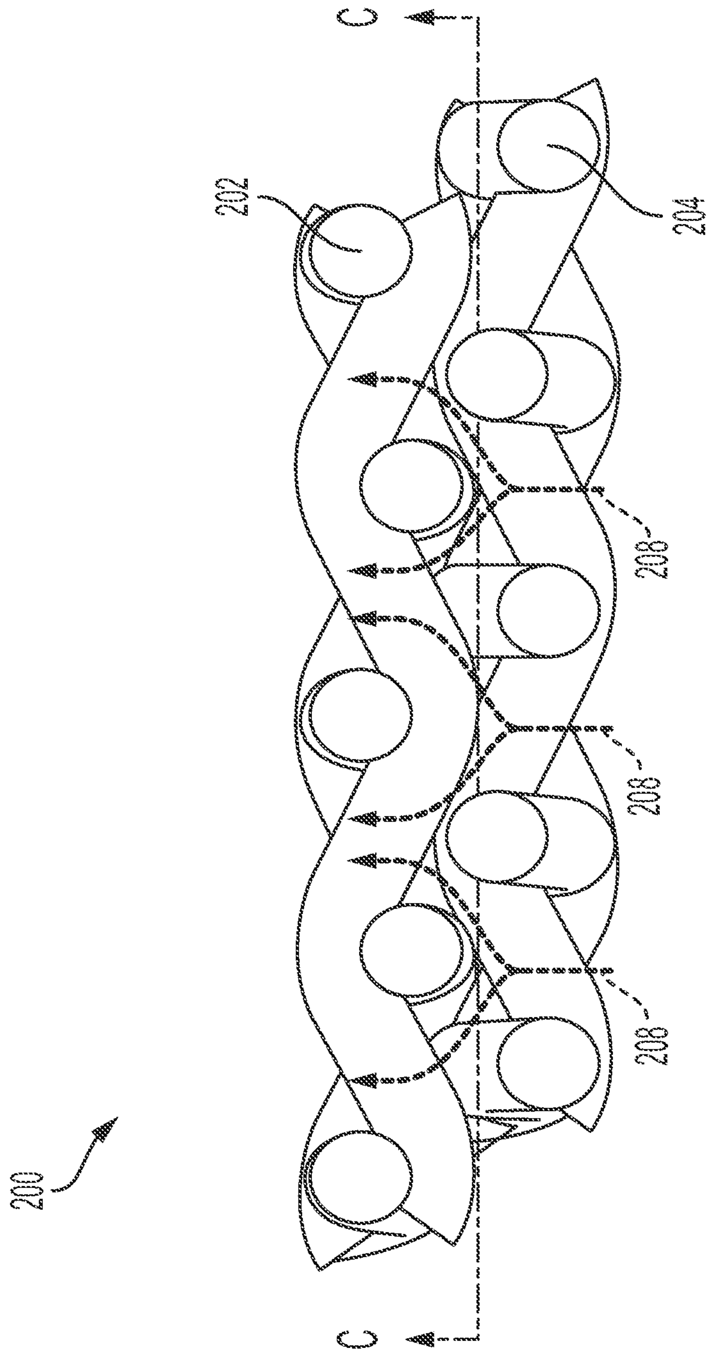
FIG. 4 shows a cross-section view along line B-B of the multilayer cell culture substrate of FIG. 3B, according to one or more embodiments.
Figure 5:
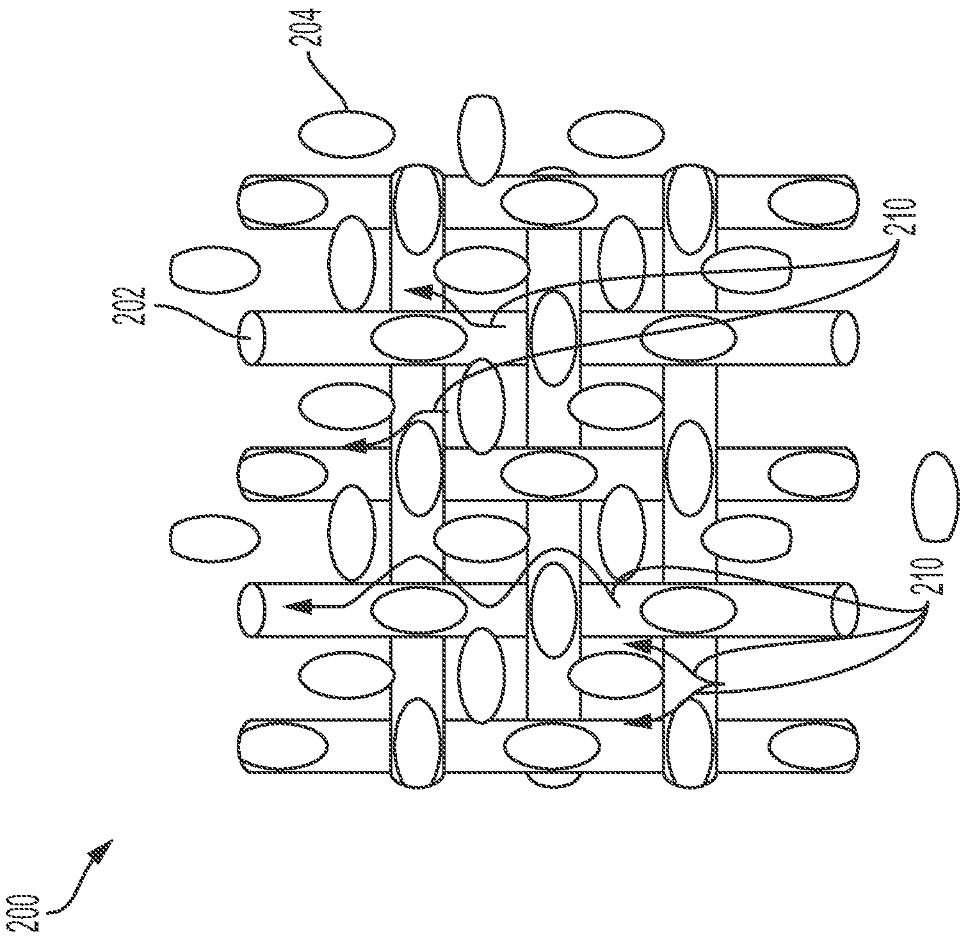
FIG. 5 shows a cross-section view along line C-C of the multilayer cell culture substrate of FIG. 4, according to one or more embodiments.

FIG. 4 shows a cross section view of the multilayer substrate 200 at line B-B in FIG. 3B. The arrows 208 show the possible fluid flow paths through openings in the second substrate layer 204 and then around filaments in the first substrate layer 202. The geometry of the mesh substrate layers is designed to allow efficient and uniform flow through one or multiple substrate layers. In addition, the structure of the matrix 200 can accommodate fluid flow through the matrix in multiple orientations. For example, as shown in FIG. 4, the direction of bulk fluid flow (as shown by arrows 208) is perpendicular to the major side surfaces of the first and second substrate layers 202 and 204. However, the matrix can also be oriented with respect to the flow such that the sides of the substrate layers are parallel to the bulk flow direction. FIG. 5 shows a cross section view of the multilayer substrate 200 along line C-C in FIG. 4, and the structure of matrix 200 allows for fluid flow (arrows 210) through fluid pathways in the multilayer substrate 200. In addition to fluid flow being perpendicular or parallel to the first and second sides of the mesh layers, the matrix can be arranged with multiple pieces of substrate at intermediate angles, or even in random arrangements with respect to fluid flow. This flexibility in orientation is enabled by the essentially isotropic flow behavior of the woven substrate. In contrast, substrates for adherent cells in existing bioreactors do not exhibit this behavior and instead their packed beds tend to create preferential flow channels and have substrate materials with anisotropic permeability. The flexibility of the matrix of the current disclosure allows for its use in various applications and bioreactor or container designs while enabling better and more uniform permeability throughout the bioreactor vessel.

With the improved structural and flow characteristics of the cell culture substrates disclosed herein, it is possible to easily and evenly distribute cells and cell culture media throughout a packed bed. However, to aid in attachment of those distributed cells to the surface of the cell culture substrate, the surface of the substrate can be modified. As discussed above, surface-modified substrates of this disclosure can include: (1) substrate surfaces with plasma-deposited positively-charged molecules; (2) silane-based amine coatings; and (3) photoactive positively charged polymer coatings. Illustrative examples of these three surface modifications will be discussed below, although embodiments of this disclosure are not intended to be limited to the specific examples below.

Plasma-Deposition of Positive Charge Molecule

According to some embodiments of this disclosure, plasma deposition is used to deposit a positively-charged molecule on the substrate surface 107. This method has many advantages. Plasma-deposited polymeric coatings can be deposited with a uniform thickness, and adhere well many substrate materials. Also, their surface properties can be controlled over a wide range by selecting suitable monomers and deposition conditions. In an example of embodiments of this disclosure, a positively-charged polymer film was deposited on a woven mesh cell culture substrate, similar to the substrate 100 in FIGS. 1A-1C, using 1,3-diaminopropane, Which comprises:

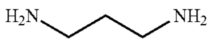

Figure 6A:
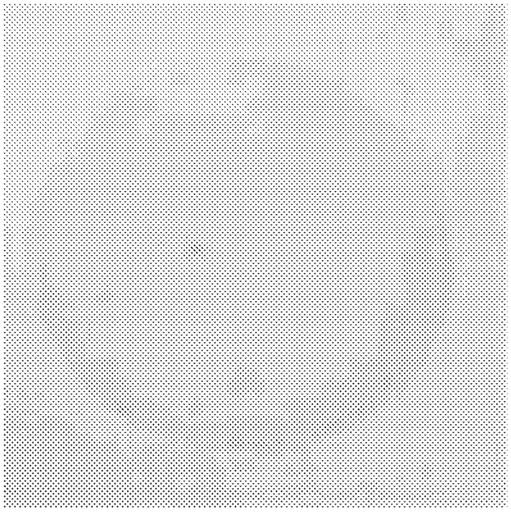
FIG. 6A is a photograph of a cell culture substrate of PET mesh without a surface treatment and stained by colloidal gold.
Figure 6B:
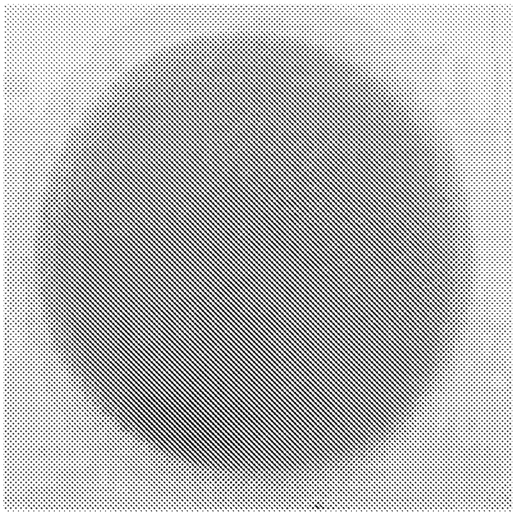
FIG. 6B is a photograph of a cell culture substrate of PET mesh whose surface is coated with positively-charged 1,3-diaminopropane plasma polymer and that is then stained by colloidal gold.
Figure 6C:
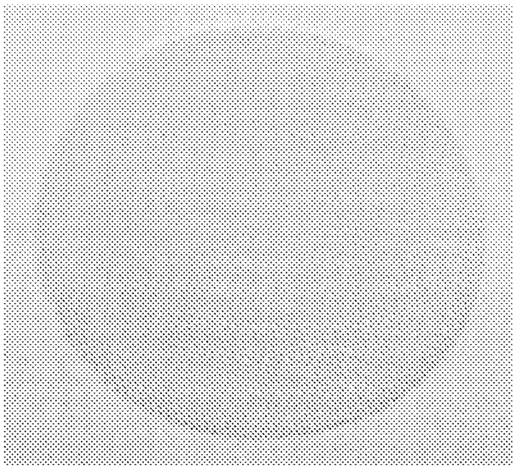
FIG. 6C is a photograph of a cell culture substrate of PET mesh without a surface treatment and stained with TBO.
Figure 6D:
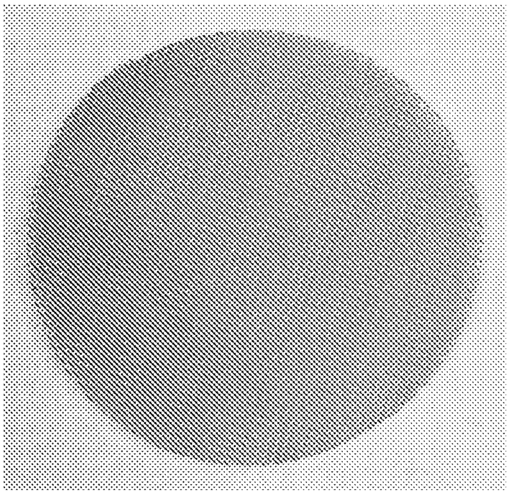
FIG. 6D is a photograph of a cell culture substrate of PET mesh whose surface is coated with negatively charged acrylic acid plasma polymer and then stained with TBO.

FIGS. 6A and 6B show a PET woven mesh cell culture substrates that have been coated with colloidal gold, Where the substrate of FIG. 6A had no surface treatment prior to staining and the substrate in FIG. 6B was coated with positively charged 1,3-diaminopropane plasma polymer prior to staining. For comparison, an untreated PET woven mesh substrate stained with Toluidine Blue O (TBO) is shown in FIG. 6C and a PET woven mesh substrate coated with negatively-charged acrylic acid plasma polymer and stained with TBO is shown in FIG. 6D. The staining shows that a significant amount of charge had been introduced on the mesh surface and the charge was uniform across the mesh.

Figure 7A:
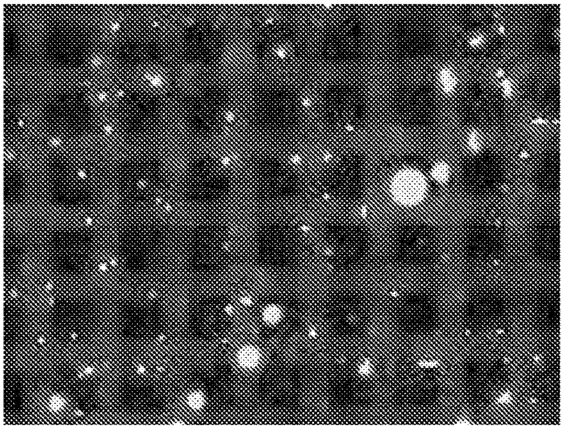
FIG. 7A is an image showing calcein staining of HEK293 cells on a cell culture substrate of PET mesh whose surface is untreated.
Figure 7B:
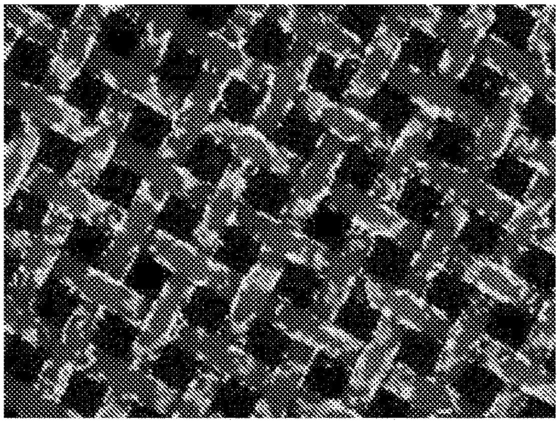
FIG. 7B is an image showing calcein staining of HEK293 cells on a cell culture substrate of PET mesh whose surface is coated with gelatin.
Figure 7C:
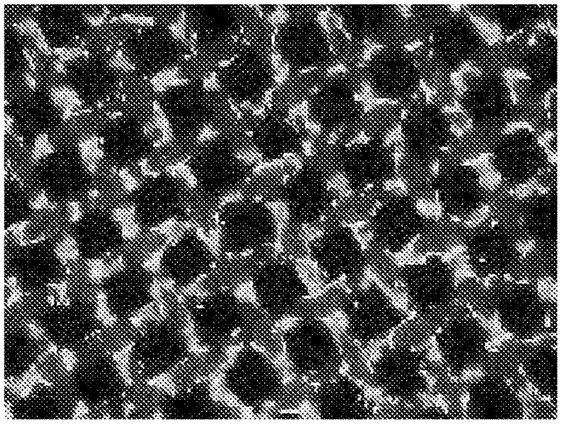
FIG. 7C is an image showing calcein staining of HEK293 cells on a cell culture substrate of PET mesh whose surface is coated with positively-charged 1,3-diaminopropane plasma polymer.
Figure 7D:
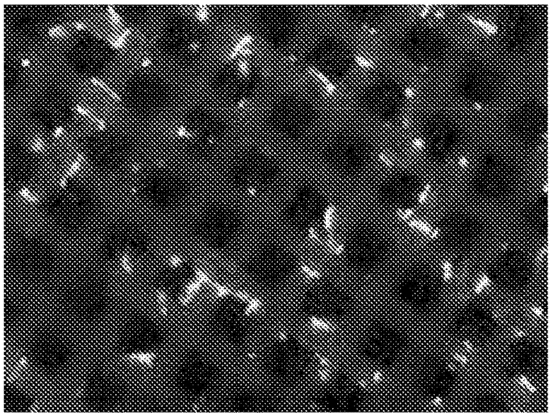
FIG. 7D is an image showing calcein staining of HEK293 on a cell culture substrate of PET mesh whose surface is coated with negatively-charged acrylic acid plasma polymer.

The treated meshes in FIG. 6 were also tested for cell attachment using HEK293 cells. FIGS. 7A-7D show the results using calcein staining of the HEK293 cells on the PET mesh substrate surfaces. FIG. 7A shows stained HEK293 cells on an untreated mesh substrate and FIG. 7B shows stained HEK293 cells on a mesh substrate coated with animal-derived gelatin. FIG. 7C shows good cell attachment was observed on the positively-charged coating, which was comparable to attachment achieved on a gelatin-coated surface (i.e., an animal-derived surface) in FIG. 7B. However, minimal attachment was observed on the negatively-charged surface from FIG. 6D, as shown in FIG. 7D. This suggests that the positively-charged surface treatment is more beneficial for the attachment of HEK293 cells. It is contemplated that similar plasma polymerization may be used to deposit other diamines or triamines to introduce positive charge on PET mesh surfaces and other cell culture surfaces of this disclosure.

For the above experiment using a surface treatment involving a plasma-deposited positively-charged molecule, the cell culture substrate was a PET woven mesh material that was cut into 32 mm diameter disks. The PET mesh disks were treated using RF plasma (Plasma Etch PE-300) at 200 w for 1 minute to help binding of the plasma polymerization coating. 1,3-diaminopropane was used as the positively-charged monomer and acrylic acid was used as the negatively-charged monomer during the plasma polymerization.

To visualize positive charge density and uniformity after the treatment, negatively charged colloidal gold (55R-PRO500 from Fitzgerald) was used to stain the treated mesh samples. Specifically, the treated mesh disks were soaked in colloidal gold suspension in a 6-well plate for 2 hours with gentle mixing. Then the mesh disks were rinsed with water before imaging. Untreated mesh disks were stained as a negative control. There was no significant staining on untreated mesh (FIG. 6A). The mesh treated with 1,3-diaminopropane plasma polymer was uniformly covered with staining (FIG. 6B), which confirmed the presence of positive charge on the mesh surface. To visualize negative charge density and uniformity of the mesh treated with acrylic acid plasma polymer, the untreated and treated disks were soaked in 0.05% Toluidine Blue O (TBO) solution in pH 11 buffer. Multiple water rinses were used to remove unbound dye. FIG. 6D show that there was significant staining on the mesh coated with acrylic acid plasma polymer, which indicated of high amount of negative charges. The coating was uniform across the mesh as well. In contrast, no significant staining was observed on untreated PET mesh in FIG. 6C.

To test cell attachment, each mesh disk was put into a well of a 6-well Ultra Low Adherent (ULA) plate. Untreated mesh disks and gelatin-coated mesh disks were used as the negative and the positive control, respectively, during the cell attachment test. The mesh disks were sanitized with 70% ethanol before cell seeding. HEK293T cells were seed at a concentration of 100,000 cell/well. ATCC 1×DMEM+10% FBS+4 mM L-Glutamine was used as culture medium. After 24 hours, Calcein staining was used to show the cell attachment. The results of the Calcein staining is shown in FIGS. 7A-7D. The cells did not significantly attach to the untreated mesh (FIG. 7A) but showed good attachment to the gelatin coated mesh (FIG. 7B). On the mesh coated with 1,3-diaminopropane plasma polymer, the cells attached very well (FIG. 7C), comparable to the gelatin-coated mesh. On the mesh coated with acryalic acid plasma polymer (FIG. 7D), cell attachment was much lower than on the mesh coated with 1,3-diaminopropane plasma polymer.

Silane-Based Amine Coating

According to some embodiments of this disclosure, the substrate surface 107 is coated with a silane-based amine coating. Silane coupling agents have the ability to form a durable bond to organic and inorganic materials. Although different silane-based amine coatings are contemplated for embodiments, an example of one molecule used in some embodiments is aminopropylsilsesquioxane (APS), the molecular structure of which is:

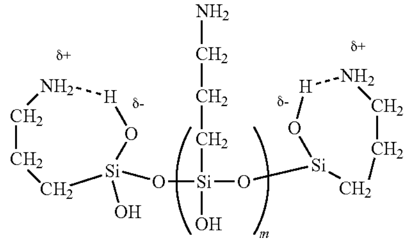

In example embodiments discussed herein, an aminopropylsilsesquioxane-water solution of different APS concentrations was used to treat PET mesh cell culture substrate surfaces through condensation of the sailanol group with the hydroxyl group on the plasma treated PET mesh substrate. Staining the mesh with negatively charged colloidal gold confirmed a uniform and positively-charged coating on the surfaces (see FIGS. 8B-8D). The coated mesh was also tested with HEK cells and demonstrated good cell attachment (see FIGS. 9A and 9B), which was comparable to a gelatin-coated surface.

For the above staining and cell attachment experiments using APS-treated substrates, the cell culture substrate was a PET woven mesh material cut into 32 mm diameter disks, as described in the above plasma-deposition coating experiment. The mesh disks were either used as-is or treated with RF plasma using Plasma Etch PE-300 at 50 W for 2 minutes. Aminopropylsilsesquioxane (APS) 25% v/v in aqueous solution was purchased from Gelest (www.gelest.com; Cas No: 29159-37-3). The solution was either used as-is or diluted to 5% or 10% v/v in water, respectively, depending on the experimental designs. For APS treatment, 3 woven mesh disks were put into 5 ml of APS solution in a plastic petri dish. The mesh disks were incubated for 30 minutes, and the samples were then washed with water and dried overnight in air.

Figure 8A:
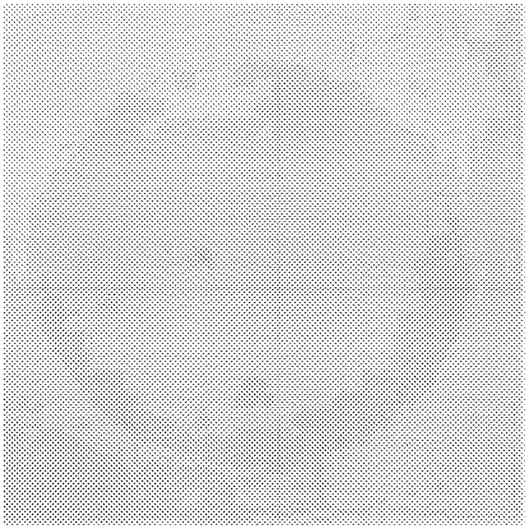
FIG. 8A is a photograph of a cell culture substrate of PET mesh without a surface treatment and stained by colloidal gold.
Figure 8B:
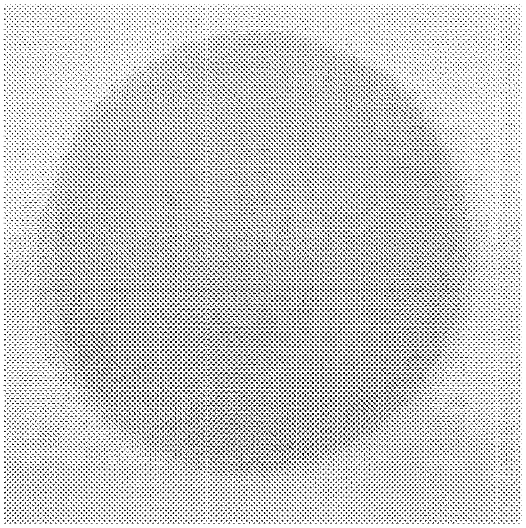
FIG. 8B is a photograph of a cell culture substrate of PET mesh whose surface is coated with a 5% APS solution and that is stained by colloidal gold.
Figure 8C:
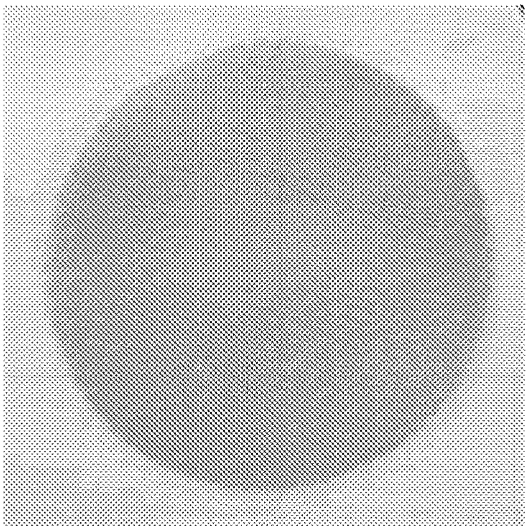
FIG. 8C is a photograph of a cell culture substrate of PET mesh whose surface is coated with a 10% APS solution and that is stained by colloidal gold.
Figure 8D:
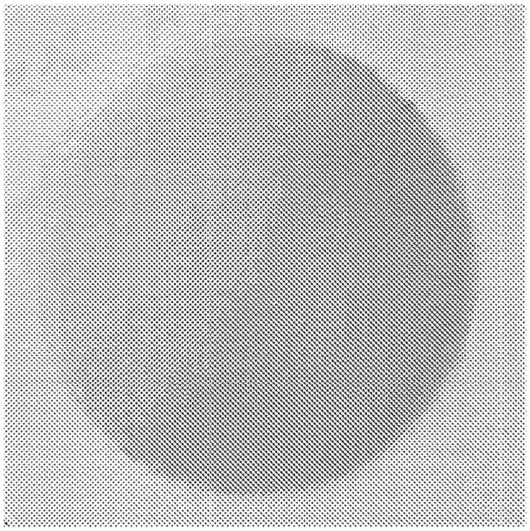
FIG. 8D is a photograph of a cell culture substrate of PET mesh whose surface is coated with a 25% APS solution and that is stained by colloidal gold.

To understand the surface charge of the woven mesh disks, the treated mesh discs were stained with negative charged colloidal gold (Fitgerald 55T-PRO550). Specifically, mesh discs were put individually into each well of a 6-well plate and 3 ml colloidal gold suspension was added to each well. For staining, the plate was placed on a rotator for 2 hours and then washed with water and imaged to visualize the staining. All the treated meshes (FIGS. 8B-8D) showed significant staining compared to the untreated mesh (FIG. 8A). There was not a significant difference between the mesh samples treated with 5%, 10%, and 25% of APS solution. Therefore, only mesh disk samples treated with 5% of APS solution were used in the cell attachment test below. In addition, new mesh disk was treated with APS at a lower concentration of 0.5% of APS solution in the cell attachment experiment below.

Figure 9A:
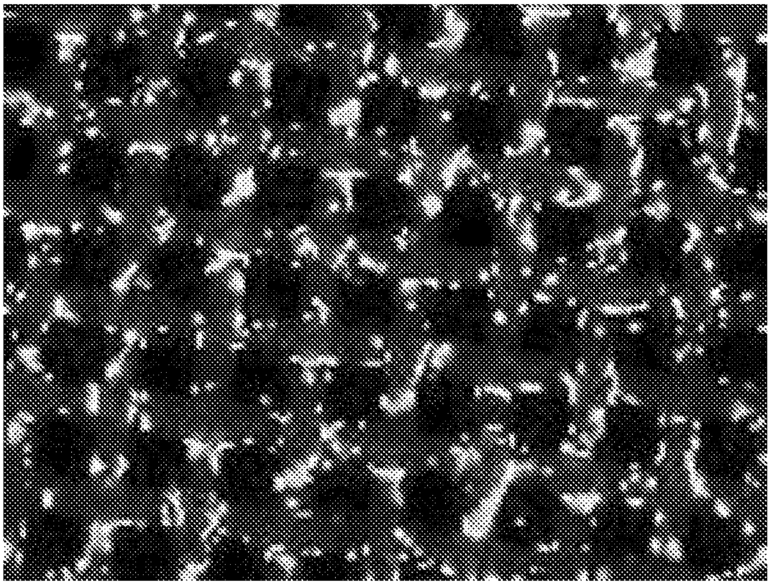
FIG. 9A is an image showing calcein staining of HEK293 cells on a cell culture substrate of PET mesh whose surface was coated by a 0.5% APS solution.
Figure 9B:
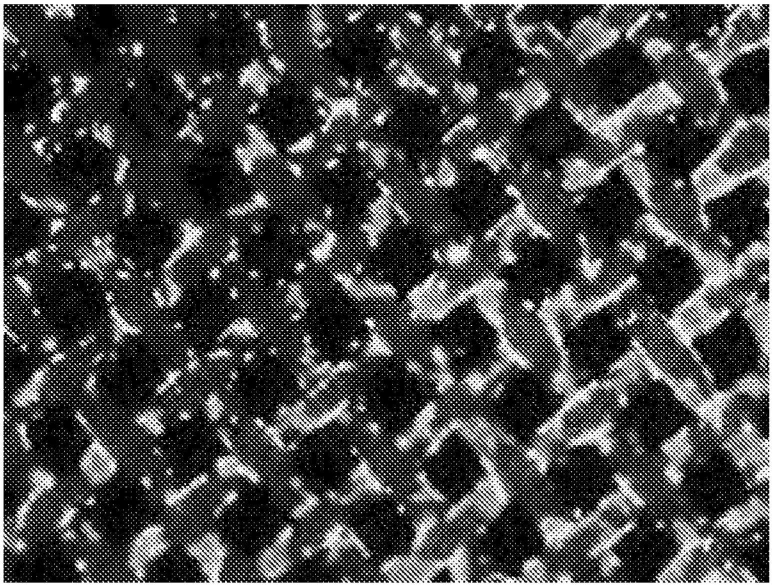
FIG. 9B is an image showing calcein staining of HEK293 cells on a cell culture substrate of PET mesh whose surface was coated by a 5% APS solution.

In the cell attachment test, each mesh disc was put into a well of a 6-well ULA plate. Untreated mesh and gelatin coated mesh were also used negative and positive controls during the cell test. The mesh disks were sanitized with 70% ethanol before cell seeding. HEK293T cells were seed at a concentration of 100,000 cell/well. ATCC 1×DMEM+10% FBS+4 mM L-Glutamine was used as culture medium. After 24 hours, calcein staining was used to show the cell attachment. FIGS. 9A and 9B show that the cell attachment for mesh disks treated with 0.5% APS and 5% APS solutions was comparable to that of gelatin coated surface (see FIG. 7B), especially for the mesh treated with the 5% APS solution, which shows somewhat more cell attachment than the mesh disk treated with 0.5% APS.

Photoactive Positive Charged Polymer Coating

According to some embodiments of this disclosure, the substrate surface 107 is coated with a photoactive positively-charged polymer coating. It is contemplated that embodiments of this disclosure can include positively-charged coatings formed using many different photoactive polymers, but in specific examples discussed herein, a photoactive positively-charged polymer coating was evaluated using two photoactive acrylamide polymers based on N-[3(4-Benzoylbenzamido)propyl] methacrylamide as the photoactive group. The polymers used in the following examples can include two polymers available from SurModics Inc. The first is Photo-acrylamide (PA04), which is a random copolymer between acrylamide (A) and N-[3(4-Benzoylbenzamido)propyl]-methacrylamide (B). The residual composition in the polymer can be represented by—ABABBAAABABABAABBABB. The second is Photo-amino-acrylamide (AP02) is a random copolymer between N-[3(4-Benzoylbenzamido)propyl]-methacrylamide-methacrylamide (B) and aminopropyl-methacrylamide (C). The residual composition in the polymer can be represented by—BCBCCBCCBBBCBCCB. These two polymers (PA04 and AP02) can be grafted on to a polymer surface after the photoactive groups are activated by ultraviolet (UV) light.

To test the positive charge coatings and cell attachment using the above photoactive polymers, 120 mg of Photo-acrylamide (PA04) was dissolved in 200 ml Milli-Q water to make 0.6 mg/ml PA04 stock solution. In addition, 80 mg of Photo-amino-acrylamide (AP02) was dissolved in 200 ml of 1 mM HCL solution to make 0.4 mg/ml AP02 solution. Working solutions for the coating were prepared according to Table 2:

TABLE 2

Preparation of solutions for coating substrate samples.

| No. | Sample | AP02 | PA04 | Water | Total Vol |
|---|---|---|---|---|---|
| 1 | AP02 0.2 mg/ml | 10 ml | — | 10 ml | 20 ml |
| 2 | AP02 0.1 mg/ml | 5 ml | — | 15 ml | 20 ml |
| 3 | AP02 0.01 mg/ml, and PA04 0.135 mg/ml | 0.5 ml | 4.5 ml | 15 ml | 20 ml |

For the staining and cell attachment experiments using photoactive polymer-treated substrates, the cell culture substrate was a PET woven mesh material cut into 32 mm diameter disks, as described in the above surface treatment experiments. The mesh disks were either used as-is or treated with RF plasma (Plasma Etch PE-300). For the photoactive polymer coating, the disks were soaked in one of above 3 sample solutions of Table 2 and exposed to UV light (5000-EC Dymax) for 160 seconds at 225 $mW/cm^2$. The disks were then removed from the solutions and rinsed with Milli-Q water 3 times.

Figure 10A:
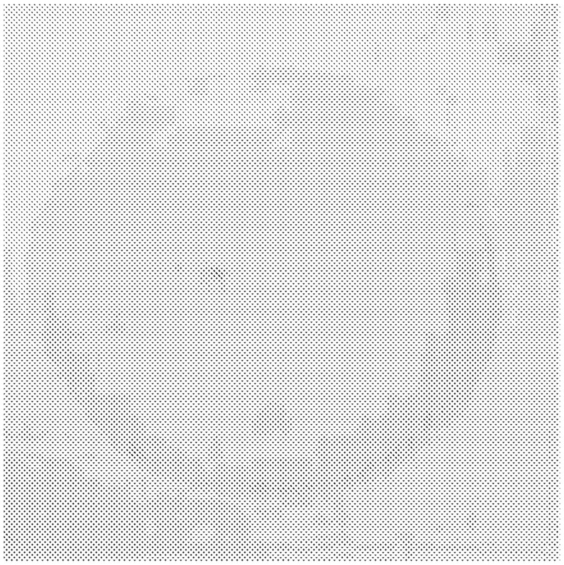
FIG. 10A is a photograph of a cell culture substrate of PET mesh without a surface treatment and stained by colloidal gold.
Figure 10B:
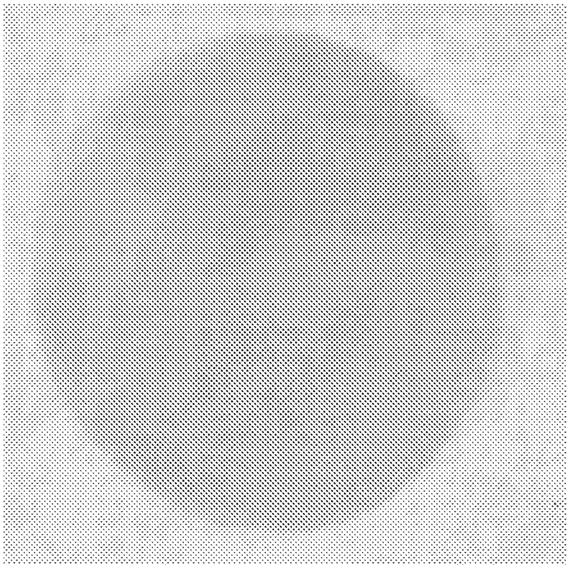
FIG. 10B is a photograph of a cell culture substrate of PET mesh whose surface is coated in 0.2 mg/mL of AP02.
Figure 10C:
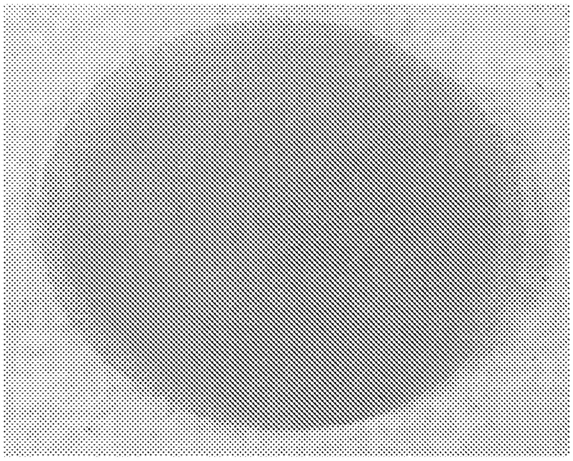
FIG. 10C is a photograph of a cell culture substrate of PET mesh whose surface is coated by a solution of 0.1 mg/mL of AP02.
Figure 10D:
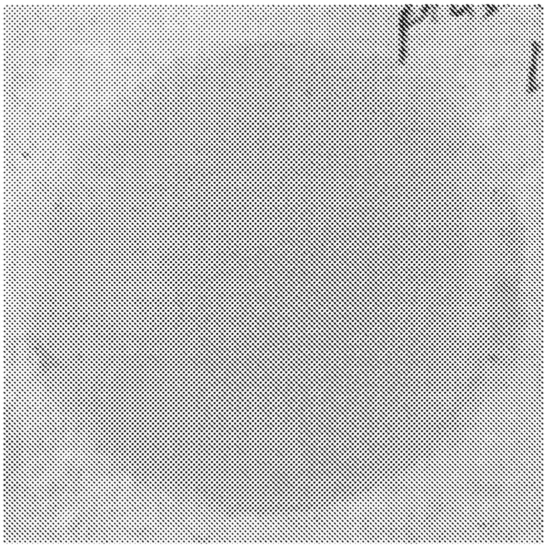
FIG. 10D is a photograph of a cell culture substrate of PET mesh whose surface is coated by a solution of a mixture of 0.01 mg/mL of AP02 and 0.1335 mg/mL of PA04.

To understand the surface charges of mesh disks treated with the photoactive polymer solutions, the treated surfaces were stained with negatively charged colloidal gold (Fitgerald 55T-PRO550). Specifically, the mesh disks were put individually into each well of a 6-well plate and 3 ml of colloidal gold suspension was added per well. For staining, the plate was placed on a rotator for 2 hours and then washed with water and imaged to visualize the staining. FIG. 10A shows the resulting staining on an uncoated sample, FIG. 10B shows staining on a sample coated using 0.2 mg/ml of APO2, FIG. 10C shows staining on a sample coated using 0.1 mg/ml of AP02, and FIG. 10D shows staining on a sample using a mixture of 0.01 mg/ml of APO2 and 0.135 mg/ml of PAO4. All of the treated mesh samples (FIGS. 10B-10D) showed significant staining compared to the untreated mesh sample (FIG. 10A). Comparing the three treated mesh samples in FIGS. 10B-10D, the one coated in a mixture of PA04 and low concentration AP02 (FIG. 10D) exhibited a lower level of staining compared to the other two coated samples (FIGS. 10B and 10C).

Figure 11A:
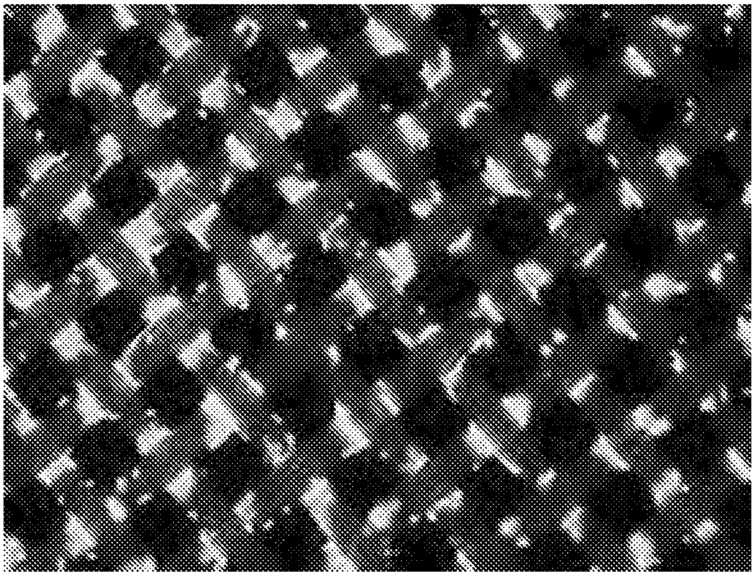
FIG. 11A is an image showing calcein staining of HEK293 cells on a cell culture substrate of PET mesh whose surface was coated by a solution of 0.1 mg/mL of AP02.
Figure 11B:
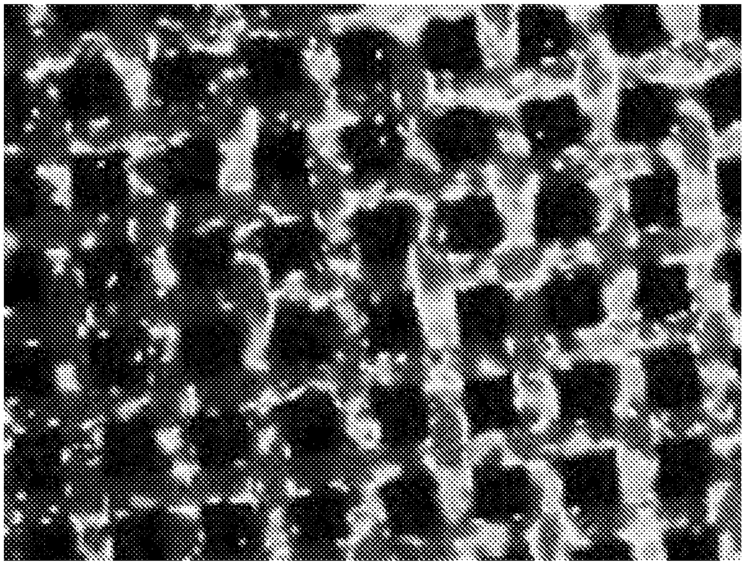
FIG. 11B is an image showing calcein staining of HEK293 cells on a cell culture substrate of PET mesh whose surface was coated by a solution of a mixture of 0.01 mg/mL of AP02 and 0.1335 mg/mL of PA04.

In a cell attachment test, only the mesh samples coated with 0.1 mg/ml of AP02 or a mixture of 0.01 mg/ml AP02 and 0.135 mg/ml PA04 were evaluated. Each mesh disk was put into a well of a 6-well ULA plate. Untreated mesh disks and gelatin-coated mesh disks were used as negative and positive controls, respectively, during the cell attachment test. The mesh disks were sanitized with 70% ethanol before cell seeding. HEK293T cells were seed at a concentration of 100,000 cell/well, and ATCC 1×DMEM+10% FBS+4 mM L-Glutamine was used as culture medium. After 24 hours, calcein staining was used to show the cell attachment on the mesh disks. As shown in FIGS. 11A and 11B, cell attachment was improved on both treated surfaces compared to an untreated surface (see FIG. 7A). However, the surface treated with a mixture of PA04 and lower concentration of AP02 exhibited better cell attachment as represented by a more uniform cell coverage on the mesh, as shown in FIG. 11B, while the mesh disk coated in 0.1 mg/ml AP02 showed cell attachment primarily in the area at the intersection of fibers, possibly because the charge distribution of the mixed coating created a more favorable surface for cell attachment.

It is contemplated that other polymers, using similar photoactive groups, can also be grafted on to polymer cell culture substrates according to some embodiments, including, but not limited to, acrylate, methacrylate, vinyl, and acrylamides, such as:

(A)

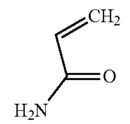

Acrylamid monomer (B)

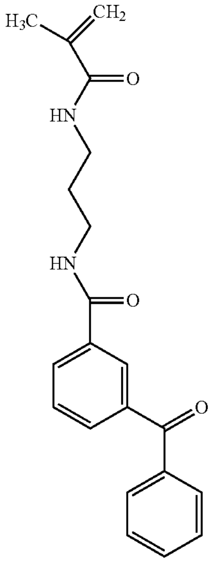

Photoactive group-methacrylamide (C)

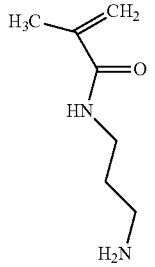

Aminopropyl-methacrylamide

In further embodiments, a cell culture substrate is coated with a polycationic polymer (such as, e.g., polyethyene imine, polyallylamine), which can be deposited and adsorb onto a plasma treated (negatively charged) cell culture substrate surface (e.g., a PET surface) or deposited on an as-is or untreated surface.

As discussed herein, the cell culture substrate can be used within a bioreactor vessel, according to one or more embodiments. For example, the substrate can be used in a packed bed bioreactor configuration, or in other configurations within a three-dimensional culture chamber. However, embodiments are not limited to a three-dimensional culture space, and it is contemplated that the substrate can be used in what may be considered a two-dimensional culture surface configuration, where the one or more layers of the substrate lay flat, such as within a flat-bottomed culture dish, to provide a culture substrate for cells. Due to contamination concerns, the vessel can be a single-use vessel that can be disposed of after use.

Figure 12:
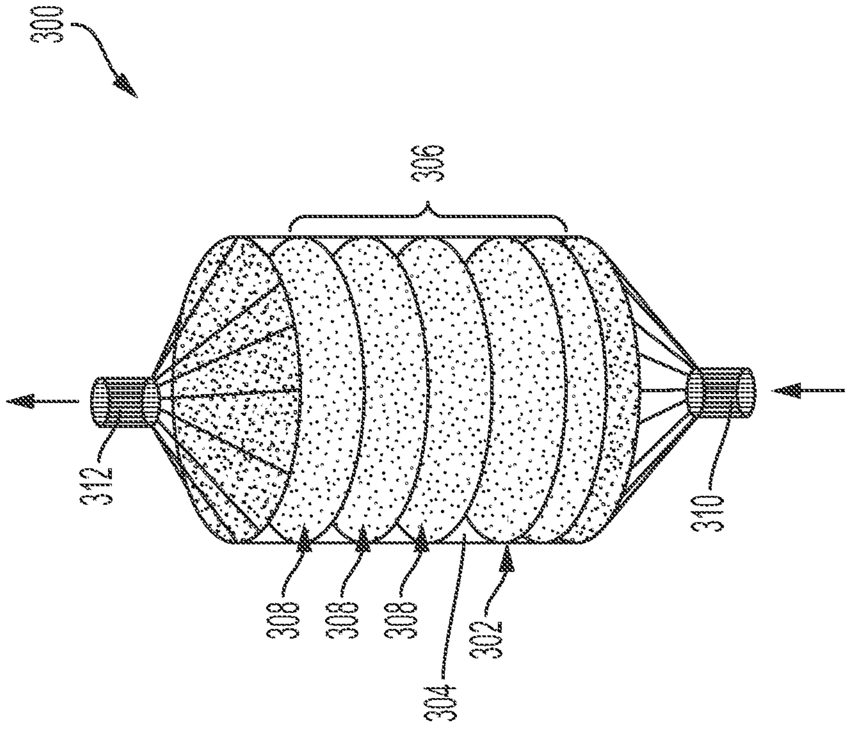
FIG. 12 shows a schematic view of a cell culture system, according to one or more embodiments.

A cell culture system is provided, according to one or more embodiments, in which the cell culture matrix is used within a culture chamber of a bioreactor vessel. FIG. 12 shows an example of a cell culture system 300 that includes a bioreactor vessel 302 having a cell culture chamber 304 in the interior of the bioreactor vessel 302. Within the cell culture chamber 304 is a cell culture matrix 306 that is made from a stack of substrate layers 308. The substrate layers 308 are stacked with the first or second side of a substrate layer facing a first or second side of an adjacent substrate layer. The bioreactor vessel 300 has an inlet 310 at one end for the input of media, cells, and/or nutrients into the culture chamber 304, and an outlet 312 at the opposite end for removing media, cells, or cell products from the culture chamber 304. By allowing stacking of substrate layers in this way, the system can be easily scaled up without negative impacts on cell attachment and proliferation, due to the defined structure and efficient fluid flow through the stacked substrates. While the vessel 300 may generally be described as having an inlet 310 and an outlet 312, some embodiments may use one or both of the inlet 310 and outlet 312 for flowing media, cells, or other contents both into and out of the culture chamber 304. For example, inlet 310 may be used for flowing media or cells into the culture chamber 304 during cell seeding, perfusion, or culturing phases, but may also be used for removing one or more of media, cells, or cell products through the inlet 310 in a harvesting phase. Thus, the terms "inlet" and "outlet" are not intended to restrict the function of those openings.

In one or more embodiments, flow resistance and volumetric density of the packed bed can be controlled by interleaving substrate layers of different geometries. In particular, mesh size and geometry (e.g., fiber diameter, opening diameter, and/or opening geometry) define the fluid flow resistance in packed bed format. By interlaying meshes of different sizes and geometries, flow resistance can be controlled or varied in one or more specific portions of the bioreactor. This will enable better uniformity of liquid perfusion in the packed bed. For example, 10 layers of Mesh A (Table 1) followed by 10 layers of Mesh B (Table 1) and followed by 10 layers of Mesh C (Table 1) can be stacked to achieve a desired packed bed characteristic. As another example, the packed bed may start with 10 layers of Mesh B, followed by 50 layers of Mesh C, followed by 10 layers of Mesh B. Such repetition pattern may continue until the full bioreactor is packed with mesh. These are examples only, and used for illustrative purposes without intending to be limiting on the possible combinations. Indeed, various combinations of meshes of different sizes are possible to obtain different profiles of volumetric density of cells growth surface and flow resistance. For example, a packed bed column with zones of varying volumetric cells densities (e.g., a series of zones creating a pattern of low/high/low/high, etc. densities) can be assembled by interleaving meshes of different sizes.

Figure 13:
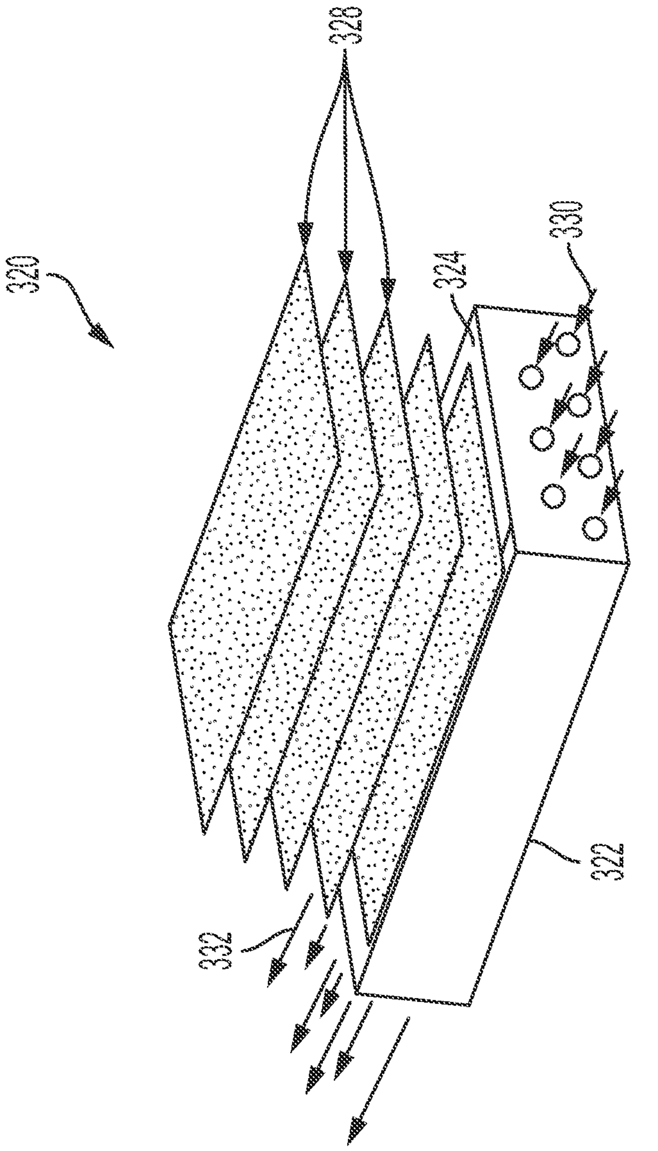
FIG. 13 shows a schematic view of a cell culture system, according to one or more embodiments.

In FIG. 12, the bulk flow direction is in a direction from the inlet 310 to the outlet 312, and, in this example, the first and second major sides of the substrate layers 308 are perpendicular to the bulk flow direction. In contrast, the example shown in FIG. 13 is of an embodiment in which the system 320 includes a bioreactor vessel 322 and stack of substrates 328 within the culture space 324 that have first and second sides that are parallel to a bulk flow direction, which corresponds to a direction shown by the flow lines into the inlets 330 and out of the outlets 332. Thus, the matrices of embodiments of this disclosure can be employed in either configuration. In each of systems 300 and 320, the substrates 308, 328 are sized and shaped to fill the interior space defined by the culture chamber 304, 324 so that the culture spaces in each vessel are filled for cell growth surfaces to maximize efficiency in terms of cells per unit volume. Although FIG. 13 shows multiple inlets 330 and multiple outlets 332, it is contemplated that the system 320 may be fed by a single inlet and have a single outlet. However, according to various embodiments herein, distribution plates can be used to help distribute the media, cells, or nutrients across a cross-section of the packed bed and thus improve uniformity of fluid flow through the packed bed. As such, the multiple inlets 330 represent how a distribution plate can be provided with a plurality of holes across the packed-bed cross-section for creating more uniform flow.

Figure 14:
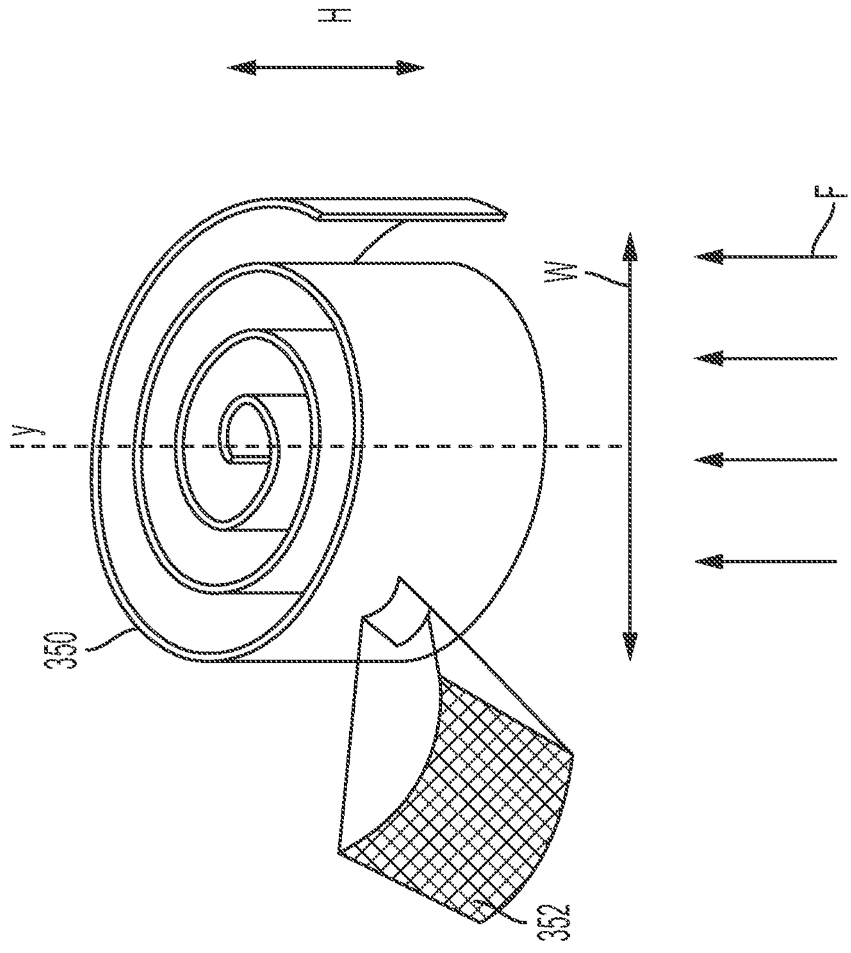
FIG. 14 shows a cell culture matrix in a rolled cylindrical configuration, according to one or more embodiments.
Figure 15:
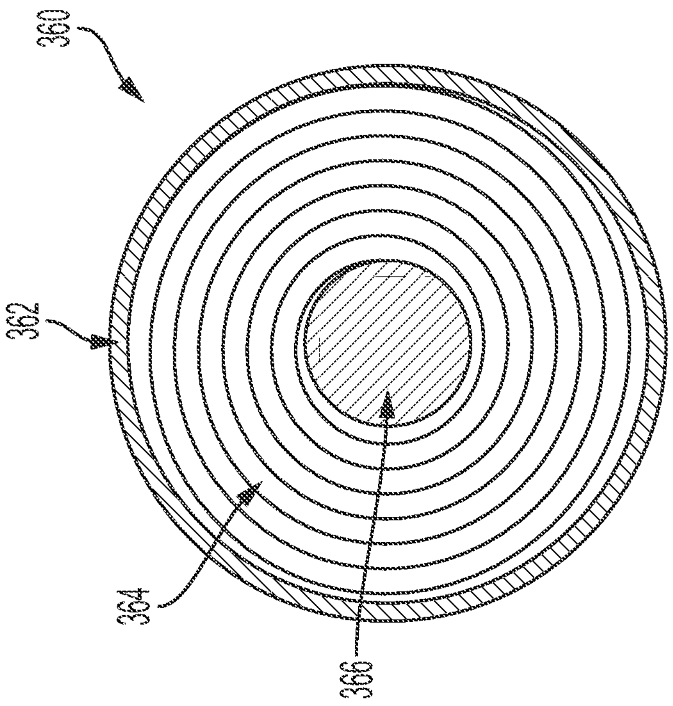
FIG. 15 shows a cell culture system incorporated a rolled cylindrical cell culture matrix, according to one or more embodiments.

FIG. 14 shows an embodiment of the matrix in which the substrate is formed into a cylindrical roll 350. For example, a sheet of a matrix material that includes a mesh substrate 352 is rolled into a cylinder about a central longitudinal axis y. The cylindrical roll 350 has a width W along a dimension perpendicular to the central longitudinal axis y and a height H along a direction perpendicular to the central longitudinal axis y. In one or more preferred embodiments, the cylindrical roll 350 is designed to be within a bioreactor vessel such that the central longitudinal axis y is parallel to a direction of bulk flow F of fluid through the bioreactor or culture chamber that houses the cylindrical roll. FIG. 15 shows a cell culture system 360 having a bioreactor vessel 362 that houses a cell culture matrix 364 in such a cylindrical roll configuration. Like the cylindrical roll 350 in FIG. 14, the cell culture matrix 364 has a central longitudinal axis, which, in FIG. 15, extends into the page. The system 360 further includes a central support member 366 around which the cell culture matrix 364 is position. The central support member 366 can be provided purely for physical support and/or alignment of the cell culture matrix 364, but can also provide other functions, according to some embodiments. For example, the central support member 366 can be provided with one or more openings for supplying media to the cell culture matrix 364 along the length H of the matrix. In other embodiments, the central support member 366 may include one or more attachment sites for holding one or more portions of the cell culture matrix 364 at the inner part of the cylindrical roll. These attachment sites may be hooks, clasps, posts, clamps, or other means of attaching the mesh sheet to the central support member 366.

Figure 16A:
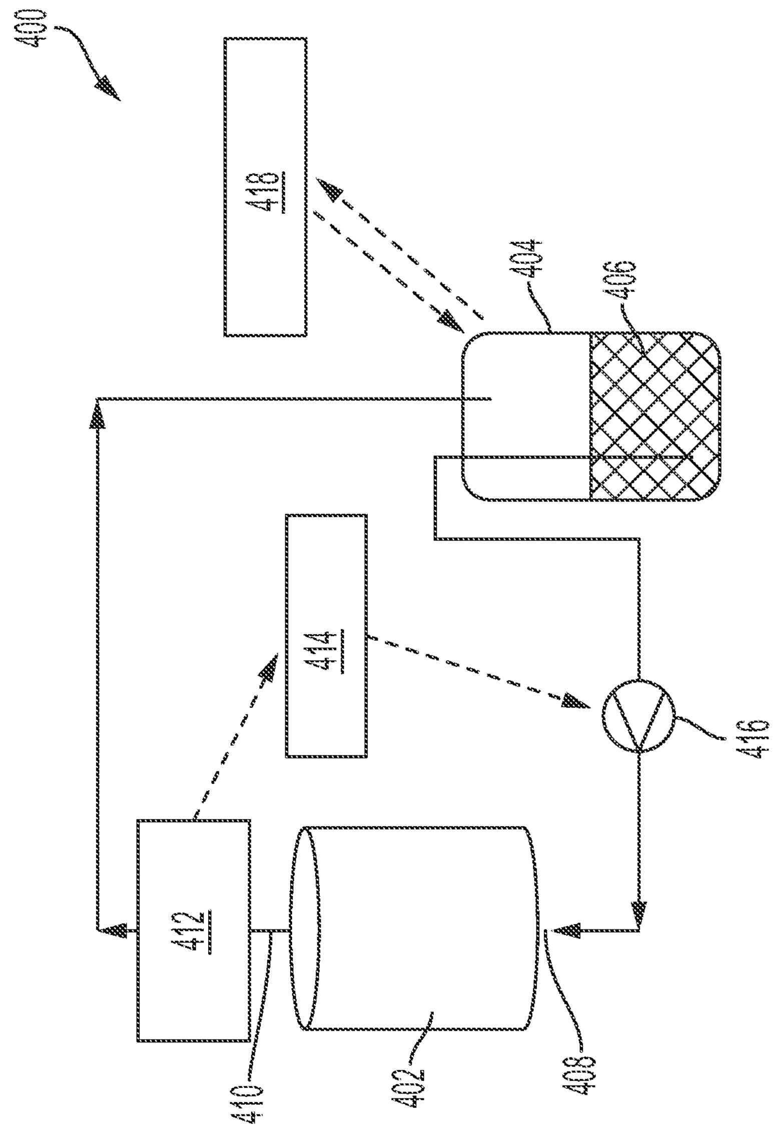
FIG. 16A is a schematic representation of a cell culture system, according to one or more embodiments.

FIG. 16A shows a cell culture system 400 according to one or more embodiments. The system 400 includes a bioreactor 402 housing the cell culture matrix of one or more embodiments disclosed herein. The bioreactor 402 can be fluidly connected to a media conditioning vessel 404, and the system is capable of supplying a cell culture media 406 within the conditioning vessel 404 to the bioreactor 402. The media conditioning vessel 404 can include sensors and control components found in typical bioreactor used in the bioprocessing industry for a suspension batch, fed-batch or perfusion culture. These include but are not limited to DO oxygen sensors, pH sensors, oxygenator/gas sparging unit, temperature probes, and nutrient addition and base addition ports. A gas mixture supplied to sparging unit can be controlled by a gas flow controller for $N_2$, $O_2$, and $CO_2$ gasses. The media conditioning vessel 404 also contains an impeller for media mixing. All media parameters measured by sensors listed above can be controlled by a media conditioning control unit 418 in communication with the media conditioning vessel 404, and capable of measuring and/or adjusting the conditions of the cell culture media 406 to the desired levels. As shown in FIG. 16A, the media conditioning vessel 404 is provided as a vessel that is separate from the bioreactor vessel 402. This can have advantages in terms of being able to condition the media separate from where the cells are cultured, and then supplying the conditioned media to the cell culture space. However, in some embodiments, media conditioning can be performed within the bioreactor vessel 402.

The media from the media 406 conditioning vessel 404 is delivered to the bioreactor 402 via an inlet 408, which may also include an injection port for cell inoculum to seed and begin culturing of cells. The bioreactor vessel 402 may also include on or more outlets 410 through which the cell culture media 406 exits the vessel 402. In addition, cells or cell products may be output through the outlet 410. To analyze the contents of the outflow from the bioreactor 402, one or more sensors 412 may be provided in the line. In some embodiments, the system 400 includes a flow control unit 414 for controlling the flow into the bioreactor 402. For example, the flow control unit 414 may receive a signal from the one or more sensors 412 (e.g., an $O_2$ sensor) and, based on the signal, adjust the flow into the bioreactor 402 by sending a signal to a pump 416 (e.g., peristaltic pump) upstream of the inlet 408 to the bioreactor 402. Thus, based on one or a combination of factors measured by the sensors 412, the pump 416 can control the flow into the bioreactor 402 to obtain the desired cell culturing conditions.

The media perfusion rate is controlled by the signal processing unit 414 that collects and compares sensors signals from media conditioning vessel 404 and sensors located at the packed bed bioreactor outlet 410. Because of the pack flow nature of media perfusion through the packed bed bioreactor 402, nutrients, pH and oxygen gradients are developed along the packed bed. The perfusion flow rate of the bioreactor can be automatically controlled by the flow control unit 414 operably connected to the peristaltic pump 416, according to the flow chart in FIG. 17A.

One or more embodiments of this disclosure offer a cell inoculation step that is different from conventional methods. In conventional methods, a pack bed with a conventional matrix is filled with culture media and concentrated inoculum is injected into the media circulation loop. The cell suspension is pumped through the bioreactor at increased flow rate to reduce nonuniformity of cell seeding via capture on the conventional packed bed matrix. In such conventional methods, the pumping of cells in the circulation loop at an elevated flow rate continues for perhaps several hours until the majority of the cells are captured in packed bed bioreactor. However, because of the nonuniform deep bed filtration nature of conventional packed bed bioreactors, cells are distributed nonuniformly inside the packed bed with the higher cell density at the inlet region of the bioreactor and lower cell density at the outlet region of the bioreactor.

In contrast, according to embodiments of the present disclosure, cell inoculum of equal volume to the void volume of the culture chamber in the bioreactor is directly injected into the packed bed through a cell inoculum injection port at the inlet 408 of the bioreactor 402 (FIG. 16A). The cell suspension is then uniformly distributed inside the packed bed because of uniform and continuous fluidic passages present in the cell culture matrix described herein. To prevent cells sedimentation due to gravity forces at the initial seeding stage, media perfusion can be started immediately after the inoculum injection. The perfusion flow rate is maintained below a preprogrammed threshold to balance the force of gravity and to avoid cells being washed from the packed bed bioreactor. Thus, at the initial cell attachment stage, cells are gently tumbled inside the packed bed and uniform cells distribution and attachment on available substrate surface is achieved.

Figure 16B:
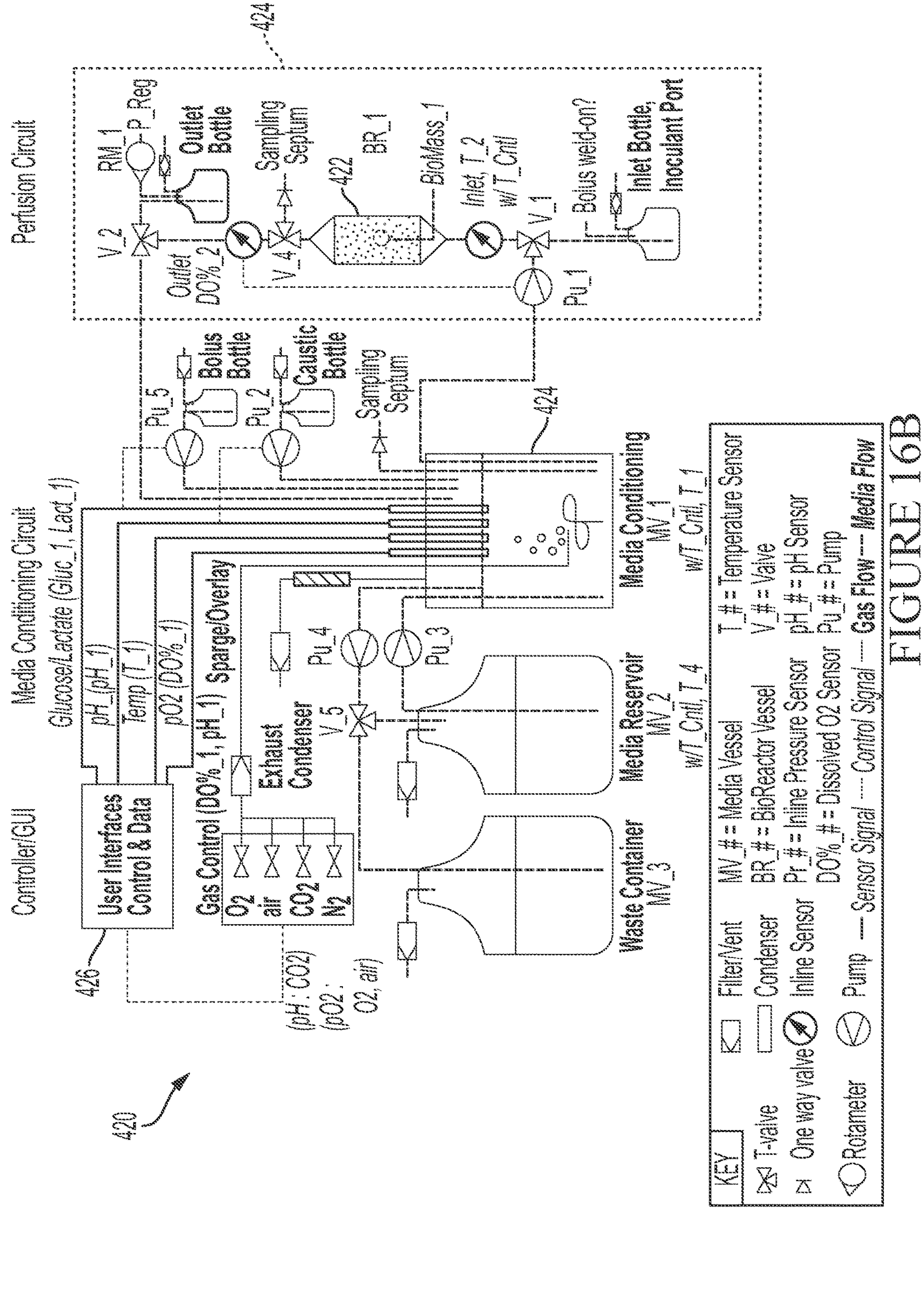
FIG. 16B is a detailed schematic of a cell culture system, according to one or more embodiments.

FIG. 16B shows a more detailed schematic of a cell culture system 420 according to one or more embodiments. The basic construction of the system 420 is similar to the system 400 in FIG. 16A, with a packed bed bioreactor 422 having a vessel containing a packed bed of cell culture material, such as a PET woven mesh, and a separate media conditioning vessel 424. In contrast to system 400, however, system 420 shows the details of the system, including sensors, user interface and controls, and various inlet and outlets for media and cells. According to some embodiments, the media conditioning vessel 424 is controlled by the controller 426 to provide the proper temperature, pH, $O_2$, and nutrients. While in some embodiments, the bioreactor 422 can also be controlled by the controller 426, in other embodiments the bioreactor 422 is provided in a separate perfusion circuit 428, where a pump is used to control the flow rate of media through the perfusion circuit 428 based on the detection of O2 at or near the outlet of the bioreactor 422.

Figure 17A:
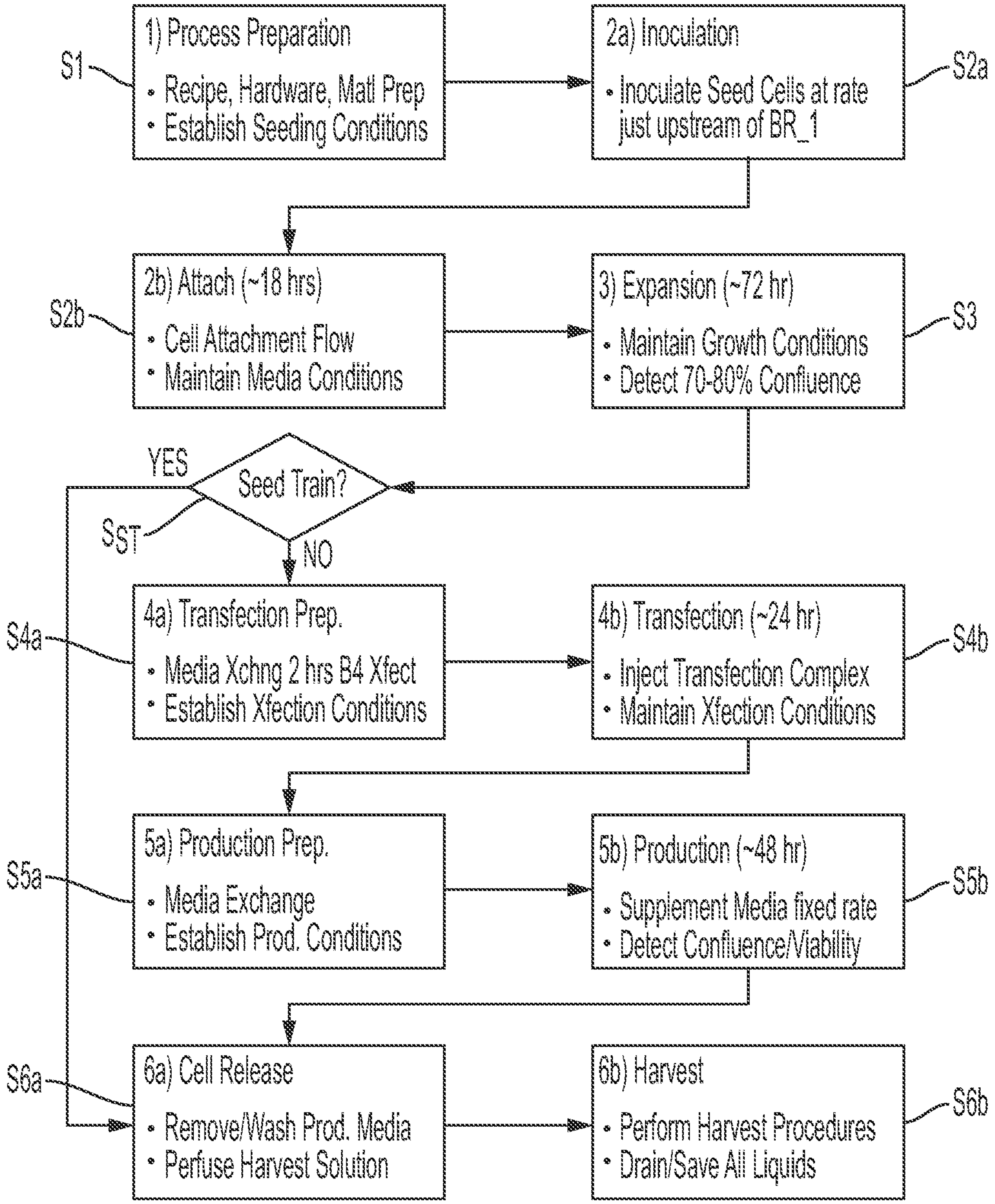
FIG. 17A shows a process flow chart for culturing cells on a cell culture system, according to one or more embodiments.

The systems of FIGS. 16A and 16B can be operated according to process steps according to one or more embodiments. As shown in FIG. 17A, these process steps can include process preparation (S1), seeding and attaching cells (S2*a*, S2*b*), cell expansion (S3), transfection (S4*a*, S4*b*), production of viral vector (S5*a*, S5*b*), and harvesting (S6*a*, S6*b*).

Figure 17B:
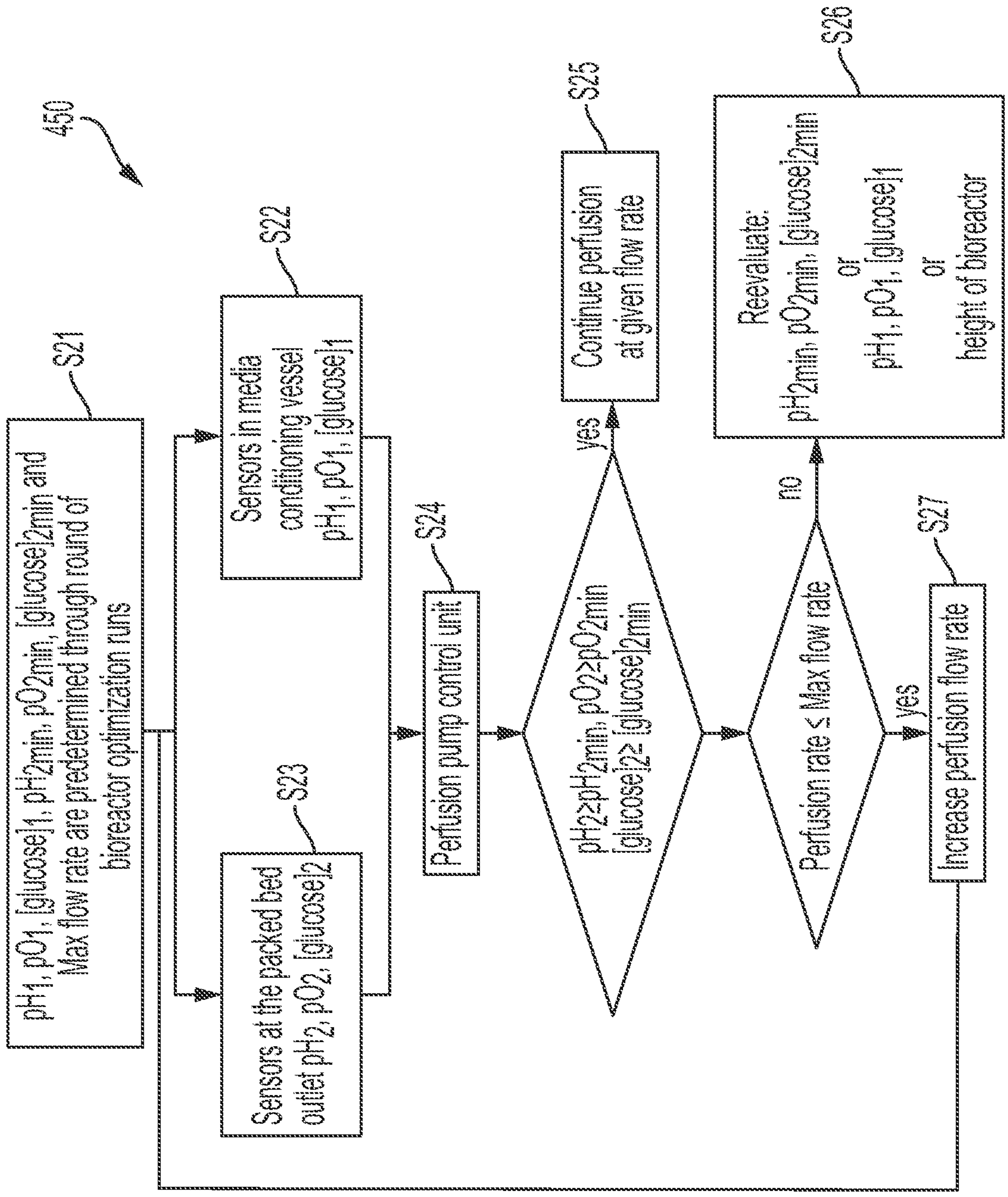
FIG. 17B shows an operation for controlling a perfusion flow rate of a cell culture system, according to one or more embodiments.

FIG. 17B shows an example of a method 450 for controlling the flow of a perfusion bioreactor system, such as the system 400 of FIG. 16A or 16B. According to the method 450, certain parameters of the system 400 are predetermined at step S21 through bioreactor optimization runs. From these optimization runs, the values of $pH_1$, $pO_1$, $[glucose]_1$, $pH_2$, $pO_2$, $[glucose]_2$, and maximum flow rate can be determined. The values for $pH_1$, $pO_1$, and $[glucose]_1$ are measured within the cell culture chamber of the bioreactor 402 at step S22, and $pH_2$, $pO_2$, and $[glucose]_2$ are measured by sensors 412 at the outlet of the bioreactor vessel 402 at step S23. Based on these values at S22 and S23, a perfusion pump control unit makes determinations at S24 to maintain or adjust the perfusion flow rate. For example, a perfusion flow rate of the cell culture media to the cell culture chamber may be continued at a present rate if at least one of $pH_2 \geq pH_{2min}$, $pO_2 \geq pO_{2min}$, and $[glucose]_2 \geq [glucose]_{2min}$ (S25). If the current flow rate is less than or equal to a predetermined max flow rate of the cell culture system, the perfusion flow rate is increased (S27). Further, if the current flow rate is not less than or equal to the predetermined max flow rate of the cell culture system, a controller of the cell culture system can reevaluate at least one of: (1) $pH_{2min}$, $pO_{2min}$, and $[glucose]_{2min}$; (2) $pH_1$, $pO_1$, and $[glucose]_1$; and (3) a height of the bioreactor vessel (S26).

The cell culture matrix can be arranged in multiple configurations within the culture chamber depending on the desired system. For example, in one or more embodiments, the system includes one or more layers of the substrate with a width extending across the width of a defined cell culture space in the culture chamber. Multiple layers of the substrate may be stacked in this way to a predetermined height. As discussed above, the substrate layers may be arranged such that the first and second sides of one or more layers are perpendicular to a bulk flow direction of culture media through the defined culture space within the culture chamber, or the first and second sides of one or more layers may be parallel to the bulk flow direction. In one or more embodiments, the cell culture matrix includes one or more substrate layers at a first orientation with respect to the bulk flow, and one or more other layers at a second orientation that is different from the first orientation. For example, various layers may have first and second sides that are parallel or perpendicular to the bulk flow direction, or at some angle in between.

In one or more embodiments, the cell culture system includes a plurality of discrete pieces of the cell culture substrate in a packed bed configuration, where the length and or width of the pieces of substrate are small relative to the culture chamber. As used herein, the pieces of substrate are considered to have a length and/or width that is small relative to the culture chamber when the length and/or width of the piece of substrate is about 50% or less of the length and/or width of the culture space. Thus, the cell culture system may include a plurality of pieces of substrate packed into the culture space in a desired arrangement. The arrangement of substrate pieces may be random or semi-random, or may have a predetermined order or alignment, such as the pieces being oriented in a substantially similar orientation (e.g., horizontal, vertical, or at an angle between 0° and 90° relative to the bulk flow direction).

The "defined culture space," as used herein, refers to a space within the culture chamber occupied by the cell culture matrix and in which cell seeding and/or culturing is to occur. The defined culture space can fill approximately the entirety of the culture chamber, or may occupy a portion of the space within the culture chamber. As used herein, the "bulk flow direction" is defined as a direction of bulk mass flow of fluid or culture media through or over the cell culture matrix during the culturing of cells, and/or during the inflow or outflow of culture media to the culture chamber.

In one or more embodiments, the cell culture matrix is secured within the culture chamber by a fixing mechanism. The fixing mechanism may secure a portion of the cell culture matrix to a wall of the culture chamber that surrounds the matrix, or to a chamber wall at one end of the culture chamber. In some embodiments, the fixing mechanism adheres a portion of the cell culture matrix to a member running through the culture chamber, such as member running parallel to the longitudinal axis of the culture chamber, or to a member running perpendicular to the longitudinal axis. However, in one or more other embodiments, the cell culture matrix may be contained within the culture chamber without being fixedly attached to the wall of the chamber or bioreactor vessel. For example, the matrix may be contained by the boundaries of the culture chamber or other structural members within the chamber such that the matrix is held within a predetermined area of the bioreactor vessel without the matrix being fixedly secured to those boundaries or structural members.

One aspect of some embodiments provides a bioreactor vessel in a roller bottle configuration. The culture chamber is capable of containing a cell culture matrix and substrate according to one or more of the embodiments described in this disclosure. In the roller bottle configuration, the bioreactor vessel may be operably attached to a means for moving the bioreactor vessel about a central longitudinal axis of the vessel. For example, the bioreactor vessel may be rotated about the central longitudinal axis. The rotation may be continuous (e.g., continuing in one direction) or discontinuous (e.g., an intermittent rotation in a single direction or alternating directions, or oscillating in back and forth rotational directions). In operation, the rotation of the bioreactor vessel causes movement of cells and/or fluid within the chamber. This movement can be considered relative with respect to the walls of the chamber. For example, as the bioreactor vessel rotates about its central longitudinal axis, gravity may cause the fluid, culture media, and/or unadhered cells to remain toward a lower portion of the chamber. However, in one or more embodiments, the cell culture matrix is essentially fixed with respect to the vessel, and thus rotates with the vessel. In one or more other embodiments, the cell culture matrix can be unattached and free to move to a desired degree relative to the vessel as the vessel rotates. The cells may adhere to the cell culture matrix, while the movement of the vessel allows the cells to receive exposure to both the cell culture media or liquid, and to oxygen or other gases within the culture chamber.

By using a cell culture matrix according to embodiments of this disclosure, such as a matrix including a woven or mesh substrate, the roller bottle vessel is provided with an increased surface area available for adherent cells to attach, proliferate, and function. In particular, using a substrate of a woven mesh of monofilament polymer material within the roller bottle, the surface area may increase by of about 2.4 to about 4.8 times, or to about 10 times that of a standard roller bottle. As discussed herein, each monofilament strand of the mesh substrate is capable of presenting itself as 2D surface for adherent cells to attach. In addition, multiple layers of mesh can we arranged in roller bottle, resulting in increases of total available surface area ranging from about 2 to 20 times that of a standard roller bottle. Thus, existing roller bottle facilities and processing, including cell seeding, media exchange, and cell harvesting, can be modified by the addition of the improved cell culture matrix disclosed herein, with minimal impact on existing operation infrastructure and processing steps.

The bioreactor vessel optionally includes one or more outlets capable of being attached to inlet and/or outlet means. Through the one or more outlets, liquid, media, or cells can be supplied to or removed from the chamber. A single port in the vessel may act as both the inlet and outlet, or multiple ports may be provided for dedicated inlets and outlets.

The packed bed cell culture matrix of one or more embodiments can consist of the woven cell culture mesh substrate without any other form of cell culture substrate disposed in or interspersed with the cell culture matrix. That is, the woven cell culture mesh substrate of embodiments of this disclosure are effective cell culture substrates without requiring the type of irregular, non-woven substrates used in existing solution. This enables cell culture systems of simplified design and construction, while providing a high-density cell culture substrate with the other advantages discussed herein related to flow uniformity, harvestability, etc.

Embodiments of this disclosure can achieve viral vector platforms of a practical size that can produce viral genomes on the scale of greater than about $10^{14}$ viral genomes per batch, greater than about $10^{15}$ viral genomes per batch, greater than about $10^{16}$ viral genomes per batch, greater than about $10^{17}$ viral genomes per batch, or up to or greater than about g $10^{16}$ viral genomes per batch. In some embodiments, production is about $10^{15}$ to about $10^{18}$ or more viral genomes per batch. For example, in some embodiments, the viral genome yield can be about $10^{15}$ to about $10^{16}$ viral genomes or batch, or about $10^{16}$ to about $10^{19}$ viral genomes per batch, or about $10^{16}$-$10^{18}$ viral genomes per batch, or about $10^{17}$ to about $10^{19}$ viral genomes per batch, or about $10^{18}$ to about $10^{19}$ viral genomes per batch, or about $10^{18}$ or more viral genomes per batch.

In addition, the embodiments disclosed herein enable not only cell attachment and growth to a cell culture substrate, but also the viable harvest of cultured cells. The inability to harvest viable cells is a significant drawback in current platforms, and it leads to difficulty in building and sustaining a sufficient number of cells for production capacity. According to an aspect of embodiments of this disclosure, it is possible to harvest viable cells from the cell culture substrate, including between 80% to 100% viable, or about 85% to about 99% viable, or about 90% to about 99% viable. For example, of the cells that are harvested, at least 80% are viable, at least 85% are viable, at least 90% are viable, at least 91% are viable, at least 92% are viable, at least 93% are viable, at least 94% are viable, at least 95% are viable, at least 96% are viable, at least 97% are viable, at least 98% are viable, or at least 99% are viable. Cells may be released from the cell culture substrate using, for example, trypsin, TrypLE, or Accutase.

As discussed herein, the cell culture substrates and bioreactor systems provided offer numerous advantages. For example, the embodiments of this disclosure can support the production of any of a number of viral vectors, such as AAV (all serotypes) and lentivirus, and can be applied toward in vivo and ex vivo gene therapy applications. The uniform cell seeding and distribution maximizes viral vector yield per vessel, and the designs enable harvesting of viable cells, which can be useful for seed trains consisting of multiple expansion periods using the same platform. In addition, the embodiments herein are scalable from process development scale to production scale, which ultimately saves development time and cost. The methods and systems disclosed herein also allow for automation and control of the cell culture process to maximize vector yield and improve reproducibility. Finally, the number of vessels needed to reach production-level scales of viral vectors (e.g., $10^{16}$ to $10^{18}$ AAV VG per batch) can be greatly reduced compared to other cell culture solutions.

Embodiments are not limited to the vessel rotation about a central longitudinal axis. For example, the vessel may rotate about an axis that is not centrally located with respect to the vessel. In addition, the axis of rotation may be a horizonal or vertical axis.

EXAMPLES

To demonstrate the efficacy of the cell culture matrix, cell culture systems, and related methods of this disclosure, studies were conducted on the seeding and culturing of cells, according to the following examples.

The embodiments disclosed herein have advantages over the existing platforms for cell culture and viral vector production. It is noted that the embodiments of this disclosure can be used for the production of a number of types of cells and cell byproducts, including, for example, adherent or semi-adherent cells, Human embryonic kidney (HEK) cells (such as HEK23), including transfected cells, viral vectors, such as Lentivirus (stem cells, CAR-T) and Adeno-associated virus (AAV). These are examples of some common applications for a bioreactor or cell culture substrate as disclosed herein, but are not intended to be limiting on the use or applications of the disclosed embodiments, as a person of ordinary skill in the art would understand the applicability of the embodiments to other uses.

Example 1

Table 3 shows examples of PET mesh samples according to some example cell culture substrate embodiments of this disclosure.

TABLE 3

Mesh substrates for permeability comparison.

| Mesh Sample | Weave Pattern | Opening Diameter (μm) | Fiber Diameter (μm) | Open area | Packing Thickness (μm) | Surface Area of 60 mm disk ($cm^2$) | Normalized Surface to Volume ratio |
|---|---|---|---|---|---|---|---|
| A | Plain | 250 | 160 | 37% | 280 | 74.9 | 1.00 |
| B | Twill | 250 | 152 | 39% | 280 | 74.2 | 0.99 |
| C | Plain | 210 | 147 | 35% | 230 | 80.9 | 1.16 |
| D | Plain | 200 | 112 | 41% | 130 | 68.1 | 1.30 |
| E | Plain | 300 | 195 | 37% | 370 | 68.1 | 0.83 |
| F | Plain | 319 | 128 | 51%* | 200 | 53.0 | 0.99 |

Illustrative Implementations

The following is a description of various aspects of implementations of the disclosed subject matter. Each aspect may include one or more of the various features, characteristics, or advantages of the disclosed subject matter. The implementations are intended to illustrate a few aspects of the disclosed subject matter and should not be considered a comprehensive or exhaustive description of all possible implementations.

Aspect 1 pertains to a cell culture substrate comprising: a substrate lattice comprising an ordered array of fibers and pores disposed between the fibers, the ordered array of fibers comprising a cell culture surface configured to support adherent or semi-adherent cells during cell culture; and a positive charge coating disposed on the cell culture surface, the positive charge coating being configured to promote adhesion of cells to the cell culture surface.

Aspect 2 pertains to the cell culture substrate of Aspect 1, wherein the positive charge coating is a polymer coating.

Aspect 3 pertains to the cell culture substrate of Aspect 1 or Aspect 2, wherein the positive charge coating is selected from a group consisting of: a plasma-deposited coating, a silane-based amine coating, and a photoactive polymer coating.

Aspect 4 pertains to the cell culture substrate of Aspect 3, wherein the positive charge coating comprises the plasma-deposited coating, the plasma-deposited coating comprising a diamine or a triamine.

Aspect 5 pertains to the cell culture substrate of Aspect 4, wherein the positive charge coating comprises 1,3-diaminopropane.

Aspect 6 pertains to the cell culture substrate of Aspect 3, wherein the positive charge coating comprises the silane-based amine coating, the silane-based amine coating comprising aminopropylsilsesquioxane (APS).

Aspect 7 pertains to the cell culture substrate of Aspect 6, wherein the silane-based amine coating is a condensate of a APS solution containing 0.5% to 25% APS v/v of water.

Aspect 8 pertains to the cell culture substrate of Aspect 3, wherein the positive charge coating comprises the photoactive polymer coating, the photoactive polymer coating comprising at least one of an acrylamide, a methacrylamide, and an aminopropyl-methacrylamide.

Aspect 9 pertains to the cell culture substrate of Aspect 3 or Aspect 8, wherein the positive charge coating comprises the photoactive polymer coating, the photoactive polymer coating comprising N-[3(4-Benzoylbenzamido)propyl]-methacrylamide.

Aspect 10 pertains to the cell culture substrate of Aspect 9, wherein the photoactive polymer coating comprises a copolymer of acrylamide and N-[3(4-Benzoylbenzamido)propyl]-methacrylamide.

Aspect 11 pertains to the cell culture substrate of Aspect 9, wherein the photoactive polymer comprises a copolymer of N-[3(4-Benzoylbenzamido)propyl]-methacrylamide and aminopropyl-methacrylamide.

Aspect 12 pertains to the cell culture substrate of any one of Aspects 8-11, wherein the photoactive polymer is grafted to the cell culture surface via exposure of the photoactive polymer to ultraviolet (UV) light.

Aspect 13 pertains to the cell culture substrate of Aspect 1 or Aspect 2, wherein the positive charge coating comprises a polycationic polymer.

Aspect 14 pertains to the cell culture substrate of Aspect 13, wherein the positive charge coating comprises at least one of polyethyeneimine and polyallylamine.

Aspect 15 pertains to the cell culture substrate of any one of Aspects 1-14, wherein the substrate lattice comprises at least one of polystyrene, polyethylene terephthalate, polycarbonate, polyvinylpyrrolidone, polybutadiene, polyvinylchloride, polyethylene oxide, polypyrroles, and polypropylene oxide.

Aspect 16 pertains to the cell culture substrate of any one of Aspects 1-15, wherein the substrate lattice comprises at least one of a molded polymer lattice sheet, a 3D-printed lattice sheet, and a woven mesh sheet.

Aspect 17 pertains to the cell culture substrate of any one of Aspects 1-16, wherein each fiber of the ordered array of fibers comprises a fiber diameter from about 50 μm to about 1000 μm, from about 50 μm to about 600 μm, from about 50 μm to about 400 μm, from about 100 μm to about 325 μm, or from about 150 μm to about 275 μm.

Aspect 18 pertains to the cell culture substrate of any one of Aspects 1-17, wherein the pores comprise a pore diameter of from about 100 μm to about 1000 μm, from about 200 μm to about 900 μm, or from about 225 μm to about 800 μm.

Aspect 19 pertains to the cell culture substrate of any one of Aspect 1-18, wherein the pores are arrayed in a regular pattern across the substrate lattice.

Aspect 20 pertains to a packed-bed bioreactor system for culturing cells, the system comprising: a vessel comprising a media inlet, a media outlet, and an interior cavity disposed between and in fluid communication with the media inlet and media outlet; a cell culture substrate disposed in the interior cavity between the media inlet and the media outlet in a packed-bed configuration, the cell culture substrate comprising a plurality of porous disks in a stacked arrangement, each of the plurality of porous disks comprises a surface configured to culture cells thereon; and a positive charge coating disposed on the surface of each of the plurality of porous disks, the positive charge coating being configured to promote adhesion of cells to the surface of the disks.

Aspect 21 pertains to the packed-bed bioreactor system of Aspect 20, wherein the positive charge coating is a polymer coating.

Aspect 22 pertains to the packed-bed bioreactor system of Aspect 20 or Aspect 21, wherein the positive charge coating is selected from a group consisting of: a plasma-deposited coating, a silane-based amine coating, and a photoactive polymer coating.

Aspect 23 pertains to the packed-bed bioreactor system of Aspect 22, wherein the positive charge coating comprises the plasma-deposited coating, the plasma-deposited coating comprising a diamine or a triamine.

Aspect 24 pertains to the packed-bed bioreactor system of Aspect 23, wherein the positive charge coating comprises 1,3-diaminopropane.

Aspect 25 pertains to the packed-bed bioreactor system of Aspect 22, wherein the positive charge coating comprises the silane-based amine coating, the silane-based amine coating comprising aminopropylsilsesquioxane (APS).

Aspect 26 pertains to the packed-bed bioreactor system of Aspect 22, wherein the positive charge coating comprises the photoactive polymer coating, the photoactive polymer coating comprising at least one of an acrylamide, a methacrylamide, and an aminopropyl-methacrylamide.

Aspect 27 pertains to the packed-bed bioreactor system of Aspect 22 or Aspect 26, wherein the positive charge coating comprises the photoactive polymer coating, the photoactive polymer coating comprising N-[3(4-Benzoylbenzamido)propyl]-methacrylamide.

Aspect 28 pertains to the packed-bed bioreactor system of Aspect 27, wherein the photoactive polymer coating comprises a copolymer of acrylamide and N-[3(4-Benzoylbenzamido)propyl]-methacrylamide.

Aspect 29 pertains to the packed-bed bioreactor system of Aspect 27, wherein the photoactive polymer comprises a copolymer of N-[3(4-Benzoylbenzamido)propyl]-methacrylamide and aminopropyl-methacrylamide.

Aspect 30 pertains to the packed-bed bioreactor system of any of Aspects 26-29, wherein the photoactive polymer is grafted to the surface via exposure of the photoactive polymer to ultraviolet (UV) light.

Aspect 31 pertains to the packed-bed bioreactor system of Aspect 20 or Aspect 21, wherein the positive charge coating comprises a polycationic polymer.

Aspect 32 pertains to the packed-bed bioreactor system of Aspect 31, wherein the positive charge coating comprises at least one of polyethyeneimine and polyallylamine.

Aspect 33 pertains to the packed-bed bioreactor system of any of Aspects 20-32, wherein the substrate lattice comprises at least one of polystyrene, polyethylene terephthalate, polycarbonate, polyvinylpyrrolidone, polybutadiene, polyvinylchloride, polyethylene oxide, polypyrroles, and polypropylene oxide.

Aspect 34 pertains to the packed-bed bioreactor system of any of Aspects 20-33, wherein plurality of porous disks comprises at least one of a molded polymer lattice sheet, a 3D-printed lattice sheet, and a woven mesh sheet.

Aspect 35 pertains to a method of making a cell culture substrate, the method comprising: providing a substrate lattice comprising an ordered array of pores disposed between connecting members of the lattice, the connecting members comprising a cell culture surface configured to support adherent or semi-adherent cells during cell culture; depositing a polymer coating on the cell culture surface of the substrate lattice, the polymer coating having a net positive charge.

Aspect 36 pertains to the method of Aspect 35, wherein the depositing of the polymer coating comprises treating the substrate lattice using plasma.

Aspect 37 pertains to the method of Aspect 36, wherein the polymer coating comprises 1,3-diaminopropane.

Aspect 38 pertains to the method of Aspect 35, wherein the polymer coating comprises a silane-based amine coating.

Aspect 39 pertains to the method of Aspect 38, wherein the silane-based amine coating comprises aminopropylsilsesquioxane (APS).

Aspect 40 pertains to the method of Aspect 35, wherein the polymer coating comprises a photoactive polymer coating.

Aspect 41 pertains to the method of Aspect 40, wherein the photoactive polymer coating comprises at least one of an acrylamide, a methacrylamide, and an aminopropyl-methacrylamide.

Aspect 42 pertains to the method of Aspect 41, wherein the photoactive polymer coating comprises at least one of N-[3(4-Benzoylbenzamido)propyl]-methacrylamide, a copolymer of acrylamide and N-[3(4-Benzoylbenzamido)propyl]-methacrylamide, and a copolymer of N-[3(4-Benzoylbenzamido)propyl]-methacrylamide and aminopropyl-methacrylamide.

Aspect 43 pertains to the method of any of Aspects 38-42, wherein the depositing of the polymer coating comprises at least one of (1) spray-coating the substrate lattice with the polymer coating and (2) soaking the substrate lattice in a solution comprising constituents of the polymer coating.

Definitions

"Wholly synthetic" or "fully synthetic" refers to a cell culture article, such as a microcarrier or surface of a culture vessel, that is composed entirely of synthetic source materials and is devoid of any animal derived or animal sourced materials. The disclosed wholly synthetic cell culture article eliminates the risk of xenogeneic contamination.

"Include," "includes," or like terms means encompassing but not limited to, that is, inclusive and not exclusive.

"Users" refers to those who use the systems, methods, articles, or kits disclosed herein, and include those who are culturing cells for harvesting of cells or cell products, or those who are using cells or cell products cultured and/or harvested according to embodiments herein.

"About" modifying, for example, the quantity of an ingredient in a composition, concentrations, volumes, process temperature, process time, yields, flow rates, pressures, viscosities, and like values, and ranges thereof, or a dimension of a component, and like values, and ranges thereof, employed in describing the embodiments of the disclosure, refers to variation in the numerical quantity that can occur, for example: through typical measuring and handling procedures used for preparing materials, compositions, composites, concentrates, component parts, articles of manufacture, or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture.

"Optional" or "optionally" means that the subsequently described event or circumstance can or cannot occur, and that the description includes instances where the event or circumstance occurs and instances where it does not.

The indefinite article "a" or "an" and its corresponding definite article "the" as used herein means at least one, or one or more, unless specified otherwise.

Abbreviations, which are well known to one of ordinary skill in the art, may be used (e.g., "h" or "hrs" for hour or hours, "g" or "gm" for gram(s), "mL" for milliliters, and "rt" for room temperature, "nm" for nanometers, and like abbreviations).

Specific and preferred values disclosed for components, ingredients, additives, dimensions, conditions, and like aspects, and ranges thereof, are for illustration only; they do not exclude other defined values or other values within defined ranges. The systems, kits, and methods of the disclosure can include any value or any combination of the values, specific values, more specific values, and preferred values described herein, including explicit or implicit intermediate values and ranges.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that any particular order be inferred.

It will be apparent to those skilled in the art that various modifications and variations can be made without departing from the spirit or scope of the disclosed embodiments. Since modifications, combinations, sub-combinations and variations of the disclosed embodiments incorporating the spirit and substance of the embodiments may occur to persons skilled in the art, the disclosed embodiments should be construed to include everything within the scope of the appended claims and their equivalents.

What is claimed:

1. A cell culture substrate comprising:

a substrate lattice comprising an ordered array of fibers and pores disposed between the fibers, the ordered array of fibers comprising a cell culture surface configured to support adherent or semi-adherent cells during cell culture; and a positive charge coating disposed on the cell culture surface, the positive charge coating being configured to promote adhesion of cells to the cell culture surface, wherein the positive charge coating is selected from a group consisting of: a plasma-deposited coating, a silane-based amine coating, and a photoactive polymer coating.

2. The cell culture substrate of claim 1, wherein the positive charge coating comprises the plasma-deposited coating, the plasma-deposited coating comprising a diamine or a triamine.

3. The cell culture substrate of claim 2, wherein the positive charge coating comprises 1,3-diaminopropane.

4. The cell culture substrate of claim 1, wherein the positive charge coating comprises the silane-based amine coating, the silane-based amine coating comprising aminopropylsilsesquioxane (APS).

5. The cell culture substrate of claim 4, wherein the silane-based amine coating is a condensate of a APS solution containing 0.5% to 25% APS v/v of water.

6. The cell culture substrate of claim 1, wherein the positive charge coating comprises the photoactive polymer coating, the photoactive polymer coating comprising at least one of an acrylamide, a methacrylamide, and an aminopropyl-methacrylamide.

7. The cell culture substrate of claim 1, wherein the positive charge coating comprises the photoactive polymer coating, the photoactive polymer coating comprising N-[3 (4-Benzoylbenzamido) propyl]-methacrylamide.

8. The cell culture substrate of claim 7, wherein the photoactive polymer coating comprises (i) a copolymer of acrylamide and N-[3 (4-Benzoylbenzamido) propyl]-methacrylamide or (ii) a copolymer of N-[3 (4-Benzoylbenzamido) propyl]-methacrylamide and aminopropyl-methacrylamide.

9. A packed-bed bioreactor system for culturing cells, the system comprising:

a vessel comprising a media inlet, a media outlet, and an interior cavity disposed between and in fluid communication with the media inlet and media outlet;

a cell culture substrate disposed in the interior cavity between the media inlet and the media outlet in a packed-bed configuration, the cell culture substrate comprising a porous substrate comprising a surface configured to culture cells thereon; and a positive charge coating disposed on the surface of the porous substrate, the positive charge coating being configured to promote adhesion of cells to the surface, wherein the positive charge coating is selected from a group consisting of: a plasma-deposited coating, a silane-based amine coating, and a photoactive polymer coating.

10. The system of claim 9, wherein the positive charge coating comprises:

(i) the plasma-deposited coating, the plasma-deposited coating comprising a diamine or a triamine, (ii) the silane-based amine coating, the silane-based amine coating comprising aminopropylsilsesquioxane (APS), or (iii) the photoactive polymer coating, the photoactive polymer coating comprising at least one of an acrylamide, a methacrylamide, and an aminopropyl-methacrylamide.

11. The system of claim 10, wherein the positive charge coating comprises 1,3-diaminopropane.

12. The system of claim 9, wherein the positive charge coating comprises the photoactive polymer coating, the photoactive polymer coating comprising N-[3 (4-Benzoylbenzamido) propyl]-methacrylamide.

13. The system of claim 12, wherein the photoactive polymer coating comprises (i) a copolymer of acrylamide and N-[3 (4-Benzoylbenzamido) propyl]-methacrylamide, or (ii) a copolymer of N-[3 (4-Benzoylbenzamido) propyl]-methacrylamide and aminopropyl-methacrylamide.

14. A method of making a cell culture substrate, the method comprising:

providing a substrate lattice comprising an ordered array of pores disposed between connecting members of the lattice, the connecting members comprising a cell culture surface configured to support adherent or semi-adherent cells during cell culture;

depositing a polymer coating on the cell culture surface of the substrate lattice, the polymer coating having a net positive charge, wherein the depositing of the polymer coating comprises treating the substrate lattice using plasma.

15. The method of claim 14, wherein the polymer coating comprises 1,3-diaminopropane.

16. A method of making a cell culture substrate, the method comprising:

providing a substrate lattice comprising an ordered array of pores disposed between connecting members of the lattice, the connecting members comprising a cell culture surface configured to support adherent or semi-adherent cells during cell culture;

depositing a polymer coating on the cell culture surface of the substrate lattice, the polymer coating having a net positive charge, wherein the polymer coating comprises at least one of:

a photoactive polymer coating, the photoactive polymer coating comprising at least one of an acrylamide, a methacrylamide, and an aminopropyl-methacrylamide, and a silane-based amine coating.

* * * * *